United States Patent
Kadobayashi et al.

(10) Patent No.: US 8,784,112 B2
(45) Date of Patent: Jul. 22, 2014

(54) TOOTH FOR DENTAL ARCH MODEL AND METHOD FOR PRODUCING THE SAME

(71) Applicant: Kabushiki Kaisha Shofu, Kyoto (JP)

(72) Inventors: Yusei Kadobayashi, Kyoto (JP); Hirokazu Sato, Kyoto (JP); Ryuichi Yoshimoto, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 0 days.

(21) Appl. No.: 14/046,178

(22) Filed: Oct. 4, 2013

(65) Prior Publication Data

US 2014/0030685 A1     Jan. 30, 2014

Related U.S. Application Data

(63) Continuation of application No. 12/226,452, filed as application No. PCT/JP2007/057148 on Mar. 30, 2007, now abandoned.

(30) Foreign Application Priority Data

| Apr. 17, 2006 | (JP) | 2006-113082 |
| Apr. 18, 2006 | (JP) | 2006-115048 |
| May 2, 2006 | (JP) | 2006-128170 |
| May 2, 2006 | (JP) | 2006-128171 |
| May 2, 2006 | (JP) | 2006-128172 |
| May 10, 2006 | (JP) | 2006-130907 |
| May 23, 2006 | (JP) | 2006-142878 |

(51) Int. Cl.
- *G09B 23/28* (2006.01)
- *A61C 13/083* (2006.01)
- *A61C 13/09* (2006.01)

(52) U.S. Cl.
CPC ............. *G09B 23/283* (2013.01); *A61C 13/083* (2013.01); *A61C 13/09* (2013.01)
USPC .............................. 434/263; 434/262; 264/19

(58) Field of Classification Search
USPC ................................................. 434/262, 263
See application file for complete search history.

(56) References Cited

U.S. PATENT DOCUMENTS

| 2,750,670 A | * | 6/1956 | Vigg ............................. 434/264 |
| 3,971,754 A |   | 7/1976 | Jurecic |

(Continued)

FOREIGN PATENT DOCUMENTS

| EP | 0 803 241 | 10/1997 |
| EP | 1 912 194 | 4/2008 |

(Continued)

OTHER PUBLICATIONS

International Search Report issued May 15, 2007 in the International (PCT) Application PCT/JP2007/057148 of which the parent U.S. Appl. No. 12/226,452 is the U.S. National Stage.

(Continued)

*Primary Examiner* — Xuan Thai
*Assistant Examiner* — Banafsheh Hadizonooz
(74) *Attorney, Agent, or Firm* — Wenderoth, Lind & Ponack, L.L.P.

(57) ABSTRACT

The present invention relates to a tooth which is used in a dental arch model with which dental students can experience dental works in the oral cavity and practice treatments. More specifically, the present invention relates to a tooth composition for formation trainings such as abutment tooth formation and cavity preparation. Since conventionally used dental arch models have a grinding sensation different from a natural tooth, dental students having completed formation trainings such as abutment tooth formation and cavity preparation by using these conventional models are frequently puzzled to have different grinding and handling properties upon dental works in the oral cavity in practice. That is, these conventional dental arch models are largely different from a natural tooth in grinding sensation including slipperiness and easiness in grinding. A tooth for a dental arch model simulating the enamel texture and the dentin texture constituting a natural tooth whereby even the difference in grinding sensation between the enamel texture and the dentin texture constituting a natural tooth can be reproduced by forming at least the enamel portion with the use of a sintered body of an inorganic powder such as alumina.

9 Claims, 4 Drawing Sheets

(56) References Cited

U.S. PATENT DOCUMENTS

| | | | | |
|---|---|---|---|---|
| 4,772,436 | A * | 9/1988 | Tyszblat | 264/19 |
| 5,284,695 | A * | 2/1994 | Barlow et al. | 264/497 |
| 6,159,417 | A * | 12/2000 | Giordano | 264/628 |
| 6,620,861 | B1 * | 9/2003 | Nakatuka et al. | 523/212 |
| 7,655,586 | B1 * | 2/2010 | Brodkin et al. | 501/103 |
| 2003/0096214 | A1 | 5/2003 | Luthardt et al. | |
| 2006/0024651 | A1 * | 2/2006 | Davis | 434/260 |
| 2006/0024652 | A1 | 2/2006 | Ose et al. | |
| 2007/0166665 | A1 | 7/2007 | Cope | |
| 2008/0242756 | A1 | 10/2008 | Kosaka et al. | |
| 2010/0015588 | A1 | 1/2010 | Funakoshi | |

FOREIGN PATENT DOCUMENTS

| | | |
|---|---|---|
| JP | 50-90650 | 7/1975 |
| JP | 1-90068 | 6/1989 |
| JP | 5-216394 | 8/1993 |
| JP | 5-241500 | 9/1993 |
| JP | 6-40841 | 2/1994 |
| JP | 10-43209 | 2/1998 |
| JP | 2003-10209 | 1/2003 |
| JP | 2003-515429 | 5/2003 |
| JP | 2004-300066 | 10/2004 |
| JP | 2005-234250 | 9/2005 |
| JP | 2007-323052 | 12/2007 |
| WO | 2004/023435 | 3/2004 |

OTHER PUBLICATIONS

English translation of PCT Written Opinion issued Nov. 27, 2008 in International Application No. PCT/JP2007/057148.

Supplementary European Search Report dated Oct. 25, 2010 issued in connection with European Patent Application No. 07 74 0584 corresponding to parent U.S. Appl. No. 12/226,452.

Office Action issued in corresponding Japanese Patent Application dated Oct. 2, 2012.

* cited by examiner

TOOTH FOR DENTAL ARCH MODEL AND METHOD FOR PRODUCING THE SAME

TECHNICAL FIELD

The present invention relates to a tooth to be used in a dental arch model with which dental students can experience dental works in the oral cavity and practice treatments. A tooth for a dental arch model is a tooth which is used for simulation of a remedial procedure in the oral cavity or practice treatments using a dental arch model in a university. The present invention relates to a tooth which is used to experience formation trainings such as abutment tooth formation and cavity preparation by grinding the tooth, and a method for producing the same.

BACKGROUND ART

In practice dental treatments, teeth extracted from human bodies and animals have conventionally been used so as to experience the grinding sensation of a natural tooth. However, there are hygienic problems associated with extracted teeth and infection may occur if hygiene control is not sufficiently conducted. Thus it was impossible to conduct training freely. Furthermore since extracted teeth comprise a natural living material, there arises a problem of corruption and it is necessary to pay a careful attention to storage.

Therefore, there has been a need for a method which enables the experience of the grinding sensation of a tooth without using a natural tooth.

Now a tooth for a dental arch model, which is used for practice treatments in the oral cavity, is often produced using an epoxy resin or a melamine resin, and are well known in the art.

However, a tooth for a dental arch model formed of an epoxy resin or a melamine resin is in the form of a natural tooth, but exhibits a grinding sensation different from that of a natural tooth. Therefore, even when performing formation trainings such as abutment tooth formation and cavity preparation, grinding sensation and handling properties are different from those of actual dental works in the oral cavity, and thus the training effect could not be obtained.

Specifically, an epoxy resin and a melamine resin are soft. Thus there is a tendency to over grind and even when performing training using such a model tooth, the grinding may not be similar to that of a hard natural tooth.

Furthermore, a natural tooth is formed of an enamel texture and the dentin texture and an enamel texture and the dentin texture are harder than a resin, and thus the enamel texture, with which a crown portion of the dentin texture is coated, and the dentin texture have different hardnesses. As a result, in case of a transition during grinding from the enamel texture to the dentin texture, the dentin texture may be excessively ground and thus a tooth may not be satisfactorily produced.

That is, it is required that a grinding sensation varies similarly to a natural tooth in the transition part from the enamel portion to the dentin portion of a tooth for a dental arch model. Therefore as a matter of course, it is important that the enamel portion reproduces the grinding sensation of the enamel texture, while the dentin portion reproduces the grinding sensation of the dentin texture.

As a result of the need for a harder material, a composite type tooth is commercially available. However even in case of a composite type tooth, since the dentin portion and the enamel portion exhibit the same grinding sensation, the grinding sensation of the composite type tooth is different from that of a natural tooth. Therefore, even when performing formation trainings such as abutment tooth formation and cavity preparation, the grinding sensation and handling properties are different from those in case of dental works in the oral cavity in practice, and thus the training effect could not be obtained. To state the matter clearly, the grinding sensation includes slipperiness and is substantially different from a natural tooth.

Japanese Unexamined Utility Model Publication (Kokai) 1-90068 discloses that a the enamel texture layer is formed of glass/ceramics having a Vickers hardness controlled within a range from 350 to 450, comprising a phlogopite crystal $[NaMg_3(Si_3AlO_{10})F_2]$ and a lithia-alumina-silica-based crystal ($Li_2O.Al_2O_3.2SiO_2$, $Li_2O.Al_2O_3.4SiO_2$) precipitated simultaneously; a tooth root layer is prepared in advance by adding white, red and yellow colorants to a polyol (base resin), mixing with an isocyanate prepolymer (curing agent), injecting the mixture into a silicone rubber mother mold under vacuum conditions and curing the mixture at a normal temperature; and a dentin texture recognition layer, which exists between the enamel texture layer and the tooth root layer thereby bonding both layers, and is formed of an adhesive resin having an opaque color.

However, the tooth comprising an enamel texture layer formed of a phlogopite crystal or a lithia-alumina-silica-based crystal is not well adapted for use because it feels too hard when grinding as compared with a natural tooth, and also it is not well adapted for use because the dentin texture recognition layer is formed of an adhesive resin which feels too soft when grinding.

Furthermore, the dentin layer is formed of an adhesive layer is disclosed. It is described that an enamel layer portion and a tooth root layer portion are formed and bonded. It is recognized as the dentin layer formed of a thick adhesive layer.

Japanese Unexamined Patent Publication (Kokai) No. (hereinafter referred to briefly as "JP-A-") 5-224591 discloses a tooth model which has a grinding sensation extremely similar to that of a natural tooth, and is suited for the training of practical dental grinding.

The tooth model comprises a crown portion whose surface has a Knoop hardness of at least 70 or more and a tooth root portion whose surface has a Knoop hardness of at least 10 to 40. The tooth model contains, as main components, an inorganic matter powder and a crosslinking resin in a weight ratio of 20%:80% to 70%:30%.

The above prior art discloses that "a tooth model may be formed of a raw material having any hardness, for example, metal, ceramics or a resin, or may be a cavity in view of the method for producing a tooth model and economic considerations". However, this is not a tooth model which can exhibit a difference in the grinding sensation between the enamel portion and the dentin portion.

JP-A-5-216395 discloses a tooth model which has a grinding sensation extremely similar to that of a natural tooth and is suited for the training of practical dental grinding, and a method for producing the same. The tooth model contains, as main components, a hydroxyapatitte powder having a porosity of 40 to 80% and a (meth)acrylate ester-based resin in a weight ratio of 20%:80% to 50%:50%. However, this is not a tooth model which can exhibit a difference in the grinding sensation between the enamel portion and the dentin portion.

JP-A-5-241498, JP-A-5-241499 and JP-A-5-241500 describe an inorganic filler and hydroxyapatitte filler. However, in all tooth models disclosed in these publications, a resin is used as a base material and thus the problem of the grinding sensation is not solved. They are not tooth models which can exhibit a difference in grinding sensation between the enamel portion and the dentin portion.

JP-A-2004-94049 describes an invention which provides a model tooth for dental training, which enables an accurate shape measurement with laser beam.

The specification discloses that "known materials can be used as a material constituting a surface of a crown portion of the model tooth of the present invention and there can be used porcelain materials such as ceramics; thermoplastic resin materials such as acryl, polystyrene, polycarbonate, an acrylonitrile-styrene-butadiene copolymer (ABS), polypropylene, polyethylene, and polyester; thermosetting resin materials such as melamine, urea, unsaturated polyester, phenol, and epoxy; and materials obtained by adding various organic and inorganic reinforcing fibers (for example, glass fiber, carbon fiber, pulp, synthetic resin fiber, etc.), various fillers (for example, talc, silica, mica, calcium carbonate, barium sulfate, alumina, etc.), colorants (for example, pigment, dye, etc.) and various additives (for example, weathering agents, antistatic agents, etc.) to these main raw materials". However, there is no description about preferable materials, and thus the problem of grinding sensation is not solved.

As a result of a study, the present inventors have found that it is necessary to use a sintered body of an inorganic material so as to exhibit the grinding sensation of a natural tooth. Because of the difficulty in controlling a hardness of an inorganic material, it is difficult to form an enamel portion and a dentin portion while controlling the hardness.

It is necessary to control a density and a particle shape of the sintered body and a sintering temperature so as to adjust the grinding sensation of the sintered body. The difference in a shrinkage rate and a thermal expansion coefficient between the enamel portion and the dentin portion upon sintering results in breaking, peeling and cracking. In addition, a gap may be formed between the dentin portion and the enamel portion. Thus, chipping may occur upon grinding and the gap gives a sensation different from the grinding sensation of a natural tooth. Thus the resultant tooth was not well adapted for use.

When a natural tooth is ground, a unique tough grinding sensation upon grinding of a living body is obtained. In particular, the dentin portion remarkably exhibits sensation of adhesion of an organic component contained in the dentinal tubule of the tooth to a bar, and sensation of inhibition of grinding.

Although various methods have been studied so as to obtain a tough grinding sensation peculiar to a natural tooth, a sufficient grinding sensation cannot be obtained using resin, composite or the like and such a sensation can not be obtained while pouring water on a conventional tooth for a dental arch model. A grinding sensation is required in which users feel a tough grinding sensation than that of an inorganic material even in case of the enamel texture because of a similar phenomenon.

However, neither a specific composition of a tooth model capable of realizing a grinding sensation of the enamel texture and the dentin texture of a natural tooth, nor a method for producing the same has been studied or reported.

A method of reproducing tooth pulp peculiar to a natural tooth has not been developed heretofore, and thus dental students could not experience exposure to tooth pulp. Dental pulp exposure (grinding down the tooth pulp portion) is the most important technique in a dental treatment. In case where tooth pulp exposure was carried out by mistake, the subsequent treatment method must be learned at the same time.

As a dental caries progresses in a natural tooth, the treatment position expands into the enamel layer, the dentin layer and the tooth pulp, and training for a root canal treatment such as a pulpectomy is most important. When a pulpectomy is carried out, since the tooth pulp is removed by a reamer and sensations of rubbing of the dentin wall surface with the reamer completely varies, training of root canal filling could not be carried out.

In a treatment of tooth pulp, a tooth designed for training of a root canal treatment is used, and also training of a root canal treatment (root canal cleaning, root canal extension, etc.) is carried out using a tooth with a small hole formed of a box-shaped acryl. However, sufficient training cannot be carried out since it is impossible to mount the tooth on a jaw and the hardness of the dentin texture varies.

It is required to develop a tooth for a dental arch model, which enables these experiences. In particular, dental students learn by hand the sensation of whether or not tooth pulp is completely removed upto the apical foramen during root canal cleaning, and thus it is difficult for beginners. Therefore, it is required to perform training using a tooth for a dental arch model in which tooth pulp in a natural tooth is reproduced.

Although removal of dental caries is an important procedure in a dental treatment, a carious dental portion is softer than a usual dentin portion and thus it is difficult to grind the carious dental portion. Therefore, it is necessary to perform training using a tooth for a dental arch model in which dental caries in a natural tooth are reproduced. It is also required to develop a method of confirming that a carious dental portion has been accurately removed.

DISCLOSURE OF THE INVENTION

An object of the present invention is to provide a tooth for a dental arch model, which enables the experience of a sensation similar to that in treating a natural tooth. Particularly, an object of the present invention is to provide a tooth for a dental arch model in which a difference in the grinding sensation between the enamel texture and the dentin texture of a natural tooth is reproduced in a tooth for a dental arch model, comprising an enamel portion and a dentin portion.

The present invention provides a tooth for a dental arch model, comprising an enamel portion and a dentin portion, wherein the enamel portion is formed of a sintered body of an inorganic powder.

The dentin portion is formed of a sintered body of an inorganic powder, a resin, a composite, a cement material or gypsum according to the intended purposes.

Formation of the enamel portion from a sintered body of an inorganic powder enables a grinding sensation similar to those of a natural tooth and by varying in the composition of the dentin portion, it is possible to impart a grinding sensation which is different from those of the enamel portion.

A first aspect of the present invention is a tooth for a dental arch model comprising an enamel portion and a dentin portion, wherein the enamel portion and the dentin portion are formed of a sintered body of an inorganic powder.

In the tooth for a dental arch model as the first aspect of the present invention, the enamel portion and the dentin portion can be integrally molded. When the enamel portion and the dentin portion are integrally molded, two parts can be molded using a material with the same composition.

When the enamel portion and the dentin portion molded using materials each having a different composition, the two parts may be directly bonded, or the enamel portion and the dentin portion may be bonded via an adhesive layer.

A second aspect of the present invention is a tooth for a dental arch model comprising an enamel portion and a dentin portion, wherein the enamel portion is formed of a sintered body of an inorganic powder and the dentin portion is formed of a resin, a composite or a cement material.

A powder of inorganic materials such as alumina, zirconia, titanium oxide and silica can be used for the tooth for a dental arch model of the present invention, but is not limited thereto, and various inorganic powders and a mixture thereof can be used.

A composite prepared by mixing the above resin with an inorganic or organic powder can be used for the tooth for a dental arch model of the present invention.

A cement material containing polyacrylic acid and aluminosilicate as main components, capable of initiating curing by power-liquid mixing can be used for the tooth for a dental arch model of the present invention.

Gypsum can be used for the tooth for a dental arch model of the present invention.

In the tooth for a dental arch model of the present invention, when both the enamel portion and the dentin portion are formed of a sintered body of an inorganic powder, an organic resin composition, a ceramic adhesive material or glass can be used as an adhesive constituting an adhesive layer.

In the present invention, it is preferred that an inorganic powder is injection-molded using a ceramic injection molding (CIM) technique to form an enamel portion and a dentin portion.

The present tooth for a dental arch model is a substitute for a hardest natural tooth in the human body and a tooth formed from a conventional material exhibits a soft feel upon grinding, whereas, the tooth for a dental arch model according to the present invention can achieve a grinding sensation similar to that of a natural tooth. It is possible to experience the grinding sensation similar to that when using an intraoral diamond grinding material (using an air turbine) rotating at a high speed of 400,000 rpm.

Since the injection molding is contacted with a grinding material rotating at a high speed and therefore adaptability between the tooth and the jaw is important. Since adaptability between enamel and dentin is also required, a CIM technique capable of accurately forming is preferably used.

The shape of a dental crown of the tooth model is also important and it is important to serve as a target of abutment tooth formation and cavity preparation and to accurately express a raised part, fossa and cusp, and thus molding using a CIM technique is suitable.

The present invention provides a method for producing a tooth for a dental arch model, when both the enamel portion and the dentin portion are formed of a sintered body of an inorganic powder, comprising injection-molding an enamel portion and a dentin portion using a CIM technique, subjecting the resultant injection molding to degreasing and sintering steps to obtain sintered bodies of the dentin portion and the enamel portion, and bonding these sintered bodies using an adhesive.

The present invention also provides a method for producing a tooth for a dental arch model, when glass is used as an adhesive, which comprises injection-molding an enamel portion and a dentin portion using a CIM technique, laminating these injection moldings using a powder of glass interposed therebetween, subjecting the resultant laminate to degreasing and sintering steps to obtain a sintered body in which the dentin portion and the enamel portion are bonded.

In the present invention, in order to impart a tough grinding sensation peculiar to a natural tooth to the enamel portion or dentin portion and to reduce grind powder scattered upon grinding of the tooth, the enamel portion or dentin portion formed of the sintered body of an inorganic powder is impregnated with an aqueous solution of polysaccharides and a protein, a thermosoluble material such as wax, or a resin such as an acryl-based resin, a urea resin or a silicone resin.

Impregnation with a thermosetting resin or a resin containing a crosslinking agent enables a soft grinding sensation similar to those of a natural tooth when compared with the case of no impregnation. When a thermosetting resin is impregnated, a grinding sensation which an entwining sensation similar to that of a natural tooth is obtained when compared to not impregnating with such a resin. These resins are not dissolved even when water is simultaneously used, and thus the entwining sensation can be reproduced. Although the present invention can be applied to both the dentin portion and the enamel portion, it is particularly preferred to apply it to the dentin portion.

In the tooth for a dental arch model of the present invention, a tooth pulp portion can be formed in the dentin portion. The tooth pulp portion is filled with a resin, a silicone rubber, a wax or a water-soluble material.

In the tooth for a dental arch model of the present invention, a false carious dental portion can be formed between the enamel portion and the dentin portion, or at the periphery thereof. The false carious dental portion is formed of a resin or a sintered body of an inorganic powder.

According to the present invention, since grinding sensation similar to that of a natural tooth is obtained in both of the dentin portion and the enamel portion and the grinding sensation transiting from the enamel portion to the dentin portion is similar to that of a natural tooth, training of grinding a natural tooth can be easily conducted even when using a model.

According to the present invention, even when both the dentin portion and the enamel portion are formed of a sintered body of an inorganic powder, it is possible to experience grinding with a natural tooth model without a soft sensation resulting from the presence of an adhesive. It is possible to experience smooth grinding from the enamel portion to the dentin portion.

By forming an abutment tooth and cavity using the tooth for a dental arch model of the present invention, it is possible to quickly experience a grinding sensation similar to that of natural tooth and to easily experience formation. Such a formation technique can be quickly mastered.

Since the sintered body of an inorganic powder is impregnated with a viscous material such as a resin, the tooth for a dental arch model of the present invention has the effect of reducing dust scattering upon tooth grinding, and thus stains due to dust of a model can be suppressed. As an obvious consequence, dust absorption by students during training is also reduced. Since the tooth for a dental arch model of the present invention has a tough grinding sensation like a natural tooth, an entwining sensation to a diamond bar generated upon grinding of a living tooth can be reproduced.

It is also possible to experience a technique of a root canal treatment or dental crown treatment by forming a tooth pulp portion or a false carious dental portion on the tooth of the present invention.

BEST MODE FOR CARRYING OUT THE INVENTION

The tooth for a dental arch model of the present invention comprises at least an enamel portion 1 and a dentin portion 2, and the enamel portion 1 is formed of a sintered body of an inorganic powder. The dentin portion 2 is formed of a sintered body of an inorganic powder, a resin, a composite, cement or gypsum according to the intended purposes.

Figure 1:
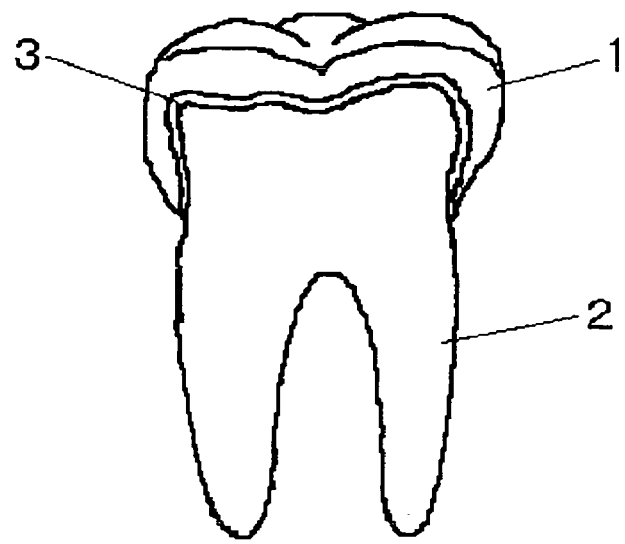
FIG. 1 is a sectional view showing a tooth for a dental arch model according to a first aspect of the present invention.

FIG. 1 shows a tooth for a dental arch model wherein both the enamel portion 1 and the dentin portion 2 are formed of a sintered body of an inorganic powder, and the enamel portion 1 and the dentin portion 2 are bonded via an adhesive layer 3. The adhesive layer 3 is composed of an adhesive such as an organic resin composition, a ceramic adhesive material or glass.

Figure 2:
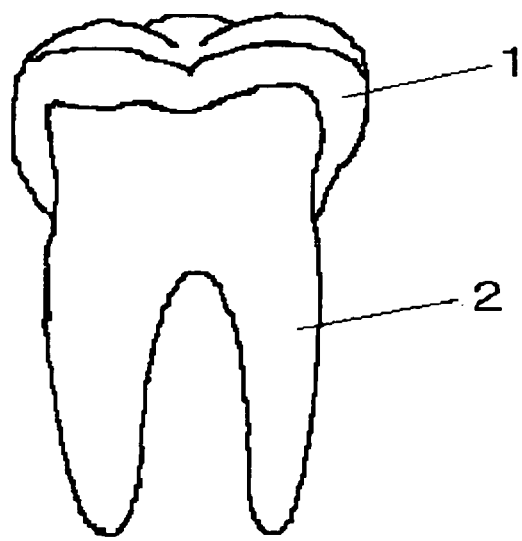
FIG. 2 is a sectional view showing a tooth for a dental arch model according to a second aspect of the present invention.

When the enamel portion 1 is formed of a sintered body of an inorganic powder and the dentin portion 2 is formed of a resin, a composite, cement or gypsum, an adhesive layer is not required (FIG. 2).

Figure 3:
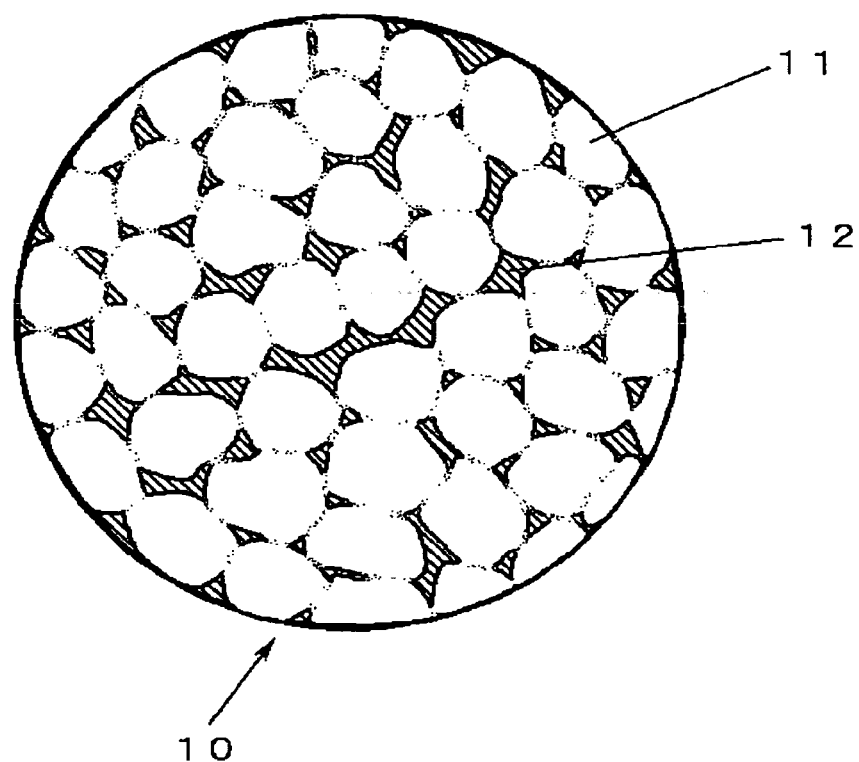
FIG. 3 is an enlarged view showing a sintered body of an inorganic powder.

In the present invention, in a sintered body of an inorganic powder 10 constituting the enamel portion 1 and the dentin portion 2, voids 12 exist between particles 11 of an inorganic powder as shown in FIG. 3. Therefore, a tough grinding sensation similar to that of a natural tooth can be reproduced by impregnating the voids 12 with a water-soluble material comprising polysaccharides or a protein, a thermosoluble material such as wax, or a resin such as an acryl-based resin, a urea resin or a silicone resin.

Figure 4:
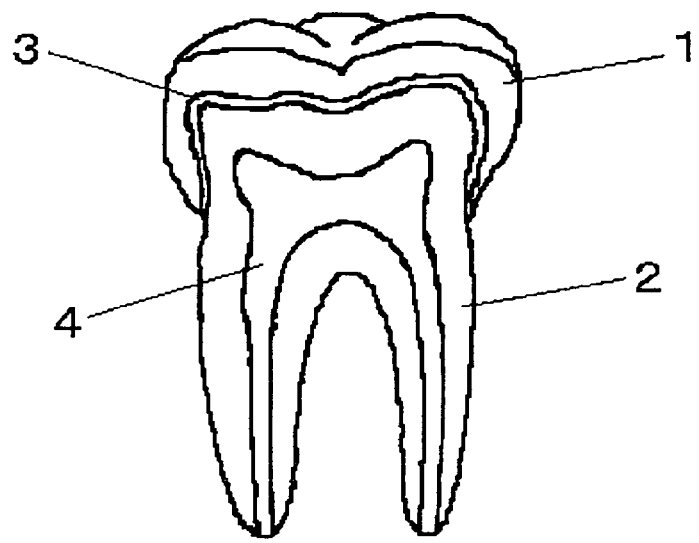
FIG. 4 is a sectional view showing a tooth for a dental arch model, which includes a tooth pulp portion, according to a first aspect of the present invention.

In the tooth for a dental arch model of the present invention, a tooth pulp portion 4 can be formed in the dentin portion 2 (FIG. 4).

In order to form the tooth pulp portion 4 in the dentin portion 2, a mold having a desired tooth pulp shape is formed using a combustible material such as an epoxy resin. The mold having a tooth pulp shape is set in a die and a dentin portion 2 is formed of an inorganic powder. The dentin portion is sintered thereby burning out the mold having a tooth pulp shape to obtain a sintered body of the dentin portion, including a space having a tooth pulp shape in the dentin portion 2. The space of the resultant tooth pulp shape in the resultant dentin portion 2 is filled with a resin, a silicone rubber, a wax or a water-soluble material to form the tooth pulp portion 4.

Figure 5:
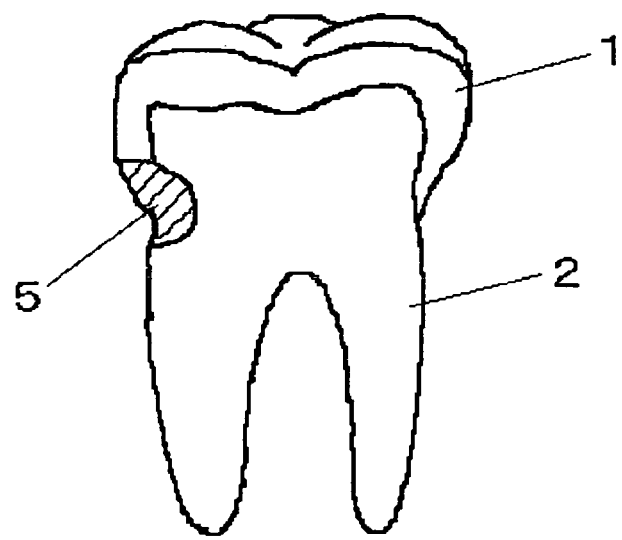
FIG. 5 is a sectional view showing a tooth for a dental arch model, which includes a false carious dental portion, according to a second aspect of the present invention.
Figure 6:
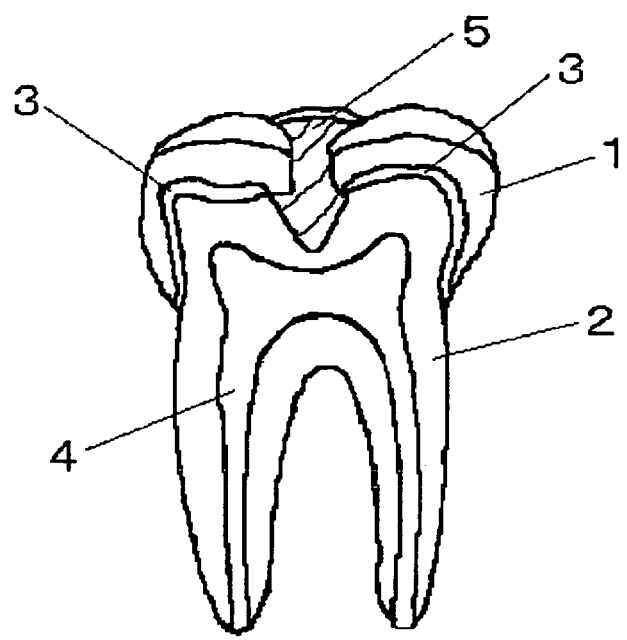
FIG. 6 is a sectional view showing a tooth for a dental arch model, which includes a tooth pulp portion and a false carious dental portion, according to a first aspect of the present invention.

In the tooth for a dental arch model of the present invention, a false carious dental portion 5 can be formed between the enamel portion 1 and the dentin portion 2, or at the periphery thereof. FIG. 5 is a schematic view in which the false carious dental portion 5 is formed at a transition part of the enamel portion 1 and the dentin portion 2 of a tooth for a dental arch model according to the second aspect. As shown in FIG. 6, the false carious dental portion 5 can be formed so as to pierce through the dentin portion from an occlusal surface of the enamel portion, and also the false carious dental portion 5 can be formed together with the tooth pulp portion 4 in the case of the tooth for a dental arch model according to the first aspect.

The false carious dental portion 5 is formed of a sintered body of an inorganic powder, a resin or a composite. When the false carious dental portion 5 is formed of the resin or composite, it is possible to visually confirm the degree of removal of the carious dental portion by adding a colorant, a fluorescent material or an X-ray contrast medium to the sintered body of an inorganic powder, the resin or composite.

Since the tooth for a dental arch model of the present invention can be colored white, ivory, milky-white or translucent by using an inorganic pigment, like a natural tooth, it is possible to experience more realistic grinding. The color is preferably white, ivory, or milky-white.

In the tooth for a dental arch model of the present invention, a jaw field and a mannequin part can be appropriately selected. It is important to carry out a procedure in order to confirm the suitability of the selection. For example, it is important to appropriately adjust the size of a tooth inserting inlet of a dental arch model.

Examples of the inorganic powder, which can be used to form the enamel portion 1 and dentin portion 2 of the present invention, include powders of alumina-based, zirconia-based, silica-based, aluminum nitride and silicon nitride ceramics, or glass. Among these, powders of alumina-based and zirconia-based ceramics are preferred.

The alumina-based or zirconia-based ceramics mean that the content of alumina or zirconia is from 60 to 100%, preferably from 80 to 100%, and more preferably from 95 to 100%, based on the composition of the sintered body. Particularly, the content of alumina is from 50 to 100%, preferably from 70 to 100%, and more preferably from 90 to 100%.

Powders of alumina-based ceramics are preferably used as the inorganic powder.

When both the enamel portion and the dentin portion are formed of a sintered body of an inorganic powder, hardnesses of the enamel portion and the dentin portion are adjusted by a method of increasing a particle size, a method of increasing voids, a method of varying the composition, a method of varying the sintering temperature, or a method of varying the retention time. The most suitable method is a method of varying the particle size while maintaining the same composition. It is possible to increase the particle size of the dentin portion when compared with the enamel portion.

It is preferred to adjust the average particle diameter of the dentin portion to an average particle diameter which is at least 10 times larger than that of the enamel portion. When the average particle diameter of the enamel portion is from 0.1 to 0.5 μm, the average particle diameter of the dentin portion is preferably adjusted within a range from 1.0 to 10.0 μm.

The sintering temperature varies depending on the composition. The sintering temperature is from 800 to 1,200° C. when a large amount of a glass component such as silica is contained. In case of alumina, the sintering temperature is from 1,200 to 1,600° C., and preferably from 1,400 to 1,550° C.

Both the enamel portion and the dentin portion are preferably formed of a sintered alumina powder. In this case, the primary particle diameter of the alumina powder is preferably from 0.2 to 5 μm. It is preferred to sinter at a sintering temperature of 1,300 to 1,600° C.

The enamel portion is preferably formed of a sintered $Al_2O_3$ powder having a primary particle diameter of 0.1 to 1.0 μm, and more preferably a sintered $Al_2O_3$ powder having a primary particle diameter of 0.2 to 0.5 μm.

The dentin portion is preferably formed of a sintered $Al_2O_3$ powder having a primary particle diameter of 0.1 to 8.0 μm, more preferably a sintered $Al_2O_3$ powder having a primary particle diameter of 2.0 to 5.0 µm, and still more preferably a sintered $Al_2O_3$ powder having a primary particle diameter of 2.0 to 3.0 µm.

The sintering temperature of the enamel portion is preferably from 1,400 to 1,600° C., and the sintering temperature of the dentin portion is preferably from 1,300 to 1,500° C. The sintering temperature has a close relation with the grinding sensation and it must be adjusted according to the particle size or raw material lot. Similarly, the retention time at a sintering temperature also has a close relation with the grinding sensation and it must be adjusted according to the particle size and raw material lot.

Vickers hardness of the enamel portion and the dentin portion is preferably from 300 to 1,000, and more preferably from 300 to 600.

As long as the grinding sensation of the alumina sintered body is not impaired, a metal oxide such as silica may be added to the tooth composition.

The enamel portion 1 and the dentin portion 2 are preferably formed by using a CIM technique which is often used as a method for forming ceramics.

The CIM technique is a technique of forming an inorganic powder and includes the following steps of:
(1) kneading alumina with a binder (which is thermally decomposed at about 1,000° C. or lower) to form pellets;
(2) making a die for an injection molding having a given shape and injection-molding the pellets obtained in the step (1);
(3) removing the binder through degreasing (decomposing a binder component by raising the temperature) after molding; and
(4) sintering the degreased injection molding at a predetermined temperature to obtain a desired sintered body.

Examples of the binder, which can be used in the present invention, include stearic acid, polyvinyl alcohol, a thermoplastic resin and wax. Stearic acid or polyvinyl alcohol is preferably used.

When the particle size of the inorganic powder is varied so as to reproduce a difference in the grinding sensation between the enamel portion and the dentin portion, there arises a difference in a shrinkage ratio during the process of degreasing pellets formed by kneading an inorganic powder with a binder and sintering the pellets. When an injection molding having a multi-layered structure of the enamel portion and the dentin portion is molded and sintered, cracking occurs at the border of the enamel portion and the dentin portion because of a difference in a shrinkage ratio, and thus sufficient bonding may not be achieved.

Therefore, when a sintered body having a layered structure of the enamel portion and the dentin portion is formed, a die must be made taking account of the shrinkage ratio so as to achieve sufficient bonding. However, it is not simple and easy.

The shrinkage ratio can be adjusted by a method of varying an amount of a binder during production of pellets, a method of varying the sintering temperature, or a method of varying the retention time. Even when the enamel portion and the dentin portion are formed of inorganic powders each having a different particle size, sufficient bonding can be achieved by unifying the shrinkage ratio of two parts. A most suited method is the method of varying an amount of a binder.

Using a CIM technique, the enamel portion 1 and the dentin portion 2 are injection-molded and, after passing through the degreasing and sintering steps, bonding can be performed using a resin or a ceramic adhesive at an interface between the sintered enamel portion and the sintered dentin portion.

As the resin for bonding in the present invention, for example, a thermoplastic resin, a thermosetting resin or a chemical polymerizable resin can be used. Among these resins, a thermosetting resin and a chemical polymerizable resin are preferred.

The thermoplastic resin means a resin which can obtain sufficient thermoplasticity for the purposes of molding by applying heat.

Specific examples of a thermoplastic resin, which can be used in the present invention, include acryl-based, styrene-based, olefin-based, vinyl chloride-based, urethane-based, polyamide-based, polybutadiene-based, polyacetal-based, unsaturated polyester-based, polycarbonate and polyphenylene ether resins.

Polysulfone-based, polyimide, polyether imide and polyether ether ketone resins can also be appropriately used. Among these resins, an acryl-based resin is particularly preferred.

A thermosetting resin means a resin which is cured by heating as a result of the progress of crosslinking. Since the thermosetting resin used for bonding in the present invention is not dissolved in a solvent after processing and is not softened even when heated again, the thermosetting resin is better than a thermoplastic resin.

A urea resin, a melamine resin, a phenol resin and an epoxy resin can be typically used, and a melamine resin and an epoxy resin are preferred. Among these, an epoxy resin is most preferred.

The chemical polymerizable resin means a resin which is polymerizable using a chemical catalyst even when it is originally included in the thermosetting resin or thermoplastic resin. A chemical polymerizable resin, which contains a crosslinking agent and has no thermoplasticity, is particularly preferred.

The ceramic adhesive used for bonding in the present invention is an adhesive which contains silicic acid and boric acid as main components and heat resistance at a sintering temperature or higher of ceramics.

Bonding required in the present invention is that the enamel portion and the dentin portion are entirely bonded. Therefore, it is not preferred that the adhesive layer partially contains a non-bonded part and large air bubbles exist since an adverse influence is exerted on the grinding sensation.

Using a CIM technique, an enamel portion 1 and a dentin portion 2 are respectively injection-molded and these injection moldings are laminated via a glass powder, followed by subjecting to degreasing and sintering steps, and thus making it possible to obtain a sintered body in which the dentin portion and the enamel portion are bonded.

When an adhesive layer for bonding an enamel portion and a dentin portion is thick, a difference in grinding sensations is felt during a transition from the enamel portion to the dentin portion. As a result, the resultant tooth model is largely different from a natural tooth.

In the tooth for a dental arch model of the present invention, the thickness of the adhesive is preferably from 1 to 500 µm, more preferably from 1 to 300 µm, still more preferably from 1 to 200 µm, and further preferably from 1 to 100 µm.

When the thickness is decreased, grinding easily transits from the enamel portion to the dentin portion, and thus the grinding sensation is similar to that of a natural tooth.

The resin used to form a dentin portion of the present invention contains a thermosetting resin and a thermoplastic resin. A thermoplastic resin or a resin containing a crosslinking agent is preferred. An epoxy resin is more preferred.

The thermoplastic resin means a resin which can obtain sufficient thermoplasticity for the purposes of molding by applying heat.

Specific examples of a thermoplastic resin, which can be used to form an enamel portion in the present invention, include acryl-based, styrene-based, olefin-based, vinyl chloride-based, urethane-based, polyamide-based, polybutadiene-based, polyacetal-based, saturated polyester-based, polycarbonate, and polyphenylene ether resins. Among these resins, acryl-based, styrene-based, urethane-based and polyamide-based resins are particularly preferred.

A preferred aspect with respect to the thermosetting resin can be obtained by mixing the thermoplastic resin with a crosslinking agent. That is, it is possible to perform training of tooth grinding without the resin being dissolved by heat generated upon grinding.

The thermosetting resin means a resin which is cured by heating as a result of the progress of polymerization.

After curing, since it is not dissolved in a solvent and is not softened even when heated again, the thermosetting resin is better than the thermoplastic resin.

The thermosetting resin, which can be used to form a dentin portion of the present invention, includes a urea resin, a melamine resin, a phenol resin and an epoxy resin. A melamine resin and an epoxy resin are preferred. An epoxy resin is most preferred.

It is also possible to use a composite prepared by mixing the resin with an inorganic or organic powder so as to improve a grinding sensation.

The inorganic powder is mainly composed of ceramic or glass and has an average particle diameter of 1.0 to 100 μm, but the composition is not particularly limited. The average particle diameter is preferably from 1.0 to 30 μm. Fine particle fillers can also be mixed.

Specific examples of the inorganic powder include powders of inorganic materials such as quartz, amorphous silica, clay, aluminum oxide, talc, mica, kaolin, glass, barium sulfate, zirconium oxide, titanium oxide, silicon nitride, aluminum nitride, titanium nitride, silicon carbide, boron carbide, calcium carbonate, hydroxyapatite and calcium phosphate. Specific examples of the organic powder include powders of polymers or oligomers such as polymethyl methacrylate, polyethyl methacrylate, polyvinyl chloride, polystyrene, polyester and nylon. Organic-inorganic composites can also be used preferably.

These powders may be used alone or in combination. It is more preferred to use powders which are surface-treated with conventionally known titanate coupling agents, aluminate coupling agents and silane coupling agents. A mixing ratio can be appropriately selected, if necessary, and may be selected from a range from 1 to 95%, and preferably from 60 to 90%.

The average particle diameter of these inorganic powders and organic powders is from 0.1 to 30 μm, preferably from 1.0 to 10 μn, and more preferably from 1.0 to 5.0 μm.

The cement material constituting the dentin portion is cured by power liquid mixing, and contains polyacrylic acid and aluminosilicate as main components.

Although a natural tooth has X-ray contrast properties, a tooth model formed of an inorganic sintered body has no X-ray contrast properties and thus it is preferred to impart X-ray contrast properties to the enamel portion and the dentin portion. X-ray contrast properties can be attained by mixing with $SrO$, $BaO$, $ZnO$, $ZrO_2$, $La_2O_3$ and other heavy metal element oxides.

A state of a cavity shape can be confirmed later using X-ray photography by imparting X-ray contrast properties to the dentin portion. A grinding state upon grinding of enamel and dentin can be found by varying X-ray contrast properties using metal to be mixed with the enamel portion and the dentin portion.

A void part exists between sintered particles constituting a sintered body of an inorganic powder. Therefore the tooth for a dental arch model of the present invention is characterized in that the void part is impregnated with a water-soluble material, a thermosoluble material or an organic material.

Any water-soluble material can be used without any limitation as long as it is a water-soluble polymer with which voids of the sintered body can be impregnated. At least one of a polysaccharide or a protein is preferably used. Among these, a protein is preferred.

When impregnated with the water-soluble material, the effect is exerted by water pouring or previously impregnating water.

Dextrin, glycogen, cellulose, pectin, konjak mannan and glucomannan, and alginic acid are preferably used as polysaccharides. Among these, cellulose, pectin, konjak mannan and glucomannan are preferred because a certain viscosity is required.

The protein may be a polymer compound consisting mainly of a polypeptide comprising about twenty kinds of L-α-amino acids. In view of the composition, a simple protein-consisting only of amino acids and a conjugated protein containing a nucleic acid, a phosphoric acid, a lipid, a saccharide and a metal are preferably used. Gelatin, an agar-based material, collagen and elastin are more preferred. Gelatin and an agar-based material are still more preferred because not only these materials easily dissolve in water, but also the shape must be retained at the void part of the sintered body.

A wax-based material can be used as the thermosoluble material with which the void part is impregnated.

When impregnated with the thermosoluble material, the effect is exerted by dissolving through frictional heat generated upon grinding. The wax exerts an effect similar to that of polysaccharides or protein without water pouring, and it is possible to easily perform training of tooth grinding without using a water pouring equipment.

As a wax, both natural wax and synthetic wax can be used. Typical examples of natural waxes include animal/vegetable wax, mineral wax and petroleum wax. As a synthetic wax, blended wax and polyethylene wax can be used, and paraffin wax is preferred. Fats and oils are also included in the wax. Fats and oils mean a glycerin ester of fatty acid and are insoluble in water and soluble in an alcohol. Fats and oils are preferably in the form of solid fat at a normal temperature (37° C., atmospheric pressure) and examples thereof include vegetable Japan tallow, animal beef tallow and lard. Specifically, lauric acid, myristic acid, palmitic acid, behenic acid, stearic acid, and fats and oils extracted from a living body can be used, and fats and oils extracted from a living body are preferred. Among these, fats and oils extracted from a living body (for example, lard, tallow, etc.) are particularly preferred.

It is possible to help impregnation by mixing a surfactant upon impregnation. That is, an auxiliary of the surfactant plays an important role so as to impregnate a void part of a sintered body with a water-soluble material or a thermosoluble material.

The surfactant can also be used as a water-soluble material.

Anionic, nonionic, cationic and amphoteric surfactants can be appropriately used. Among these surfactants, anionic and nonionic surfactants are preferred. As the anionic surfactant, a fatty acid salt (soap) $C_{11}H_{23}COONa$, an alpha-sulfo fatty acid ester salt (α-SFE) $C_{10}H_{21}$—$CH(SO_{33}Na)COOCH_3$, an alkyl benzene sulfonate (ABS) $C_{12}H_{25}$—$(C_6H_4)SO_3Na$, an alkyl sulfate (AS) [higher alcohol-based] $C_{12}H_{25}$—$OSO_3Na$, an alkyl ether sulfate ester salt (AES) $C_{12}H_{25}$—$O(CH_2CH_2O)_3SO_3Na$, and a triethanolamine alkyl sulfate $C_{12}H_{25}$—$OSO_3^-.^+NH(CH_2CH_2OH)_3$ are used.

As the nonionic surfactant, a fatty acid diethanolamide $C_{11}H_{23}$—$CON(CH_2CH_2OH)_2$, a polyoxyethylene alkyl ether (AE) $C_{12}H_{25}$—$O(CH_2CH_2O)_8H$, and a polyoxyethylene alkyl phenyl ether (APE) $C_9H_{19}$—$(C_6H_4)O(CH_2CH_2O)_8H$ are used.

As the cationic surfactant, an alkyltrimethyl ammonium salt $C_{12}H_{25}$—$N^+(CH_3)_3.Cl^-$, a dialkyldimethyl ammonium chloride $C_{12}H_{25}$—$N^+(C_8H_{17})(CH_3)_2.Cl^-$, and an alkyl pyridinium chloride $C_{12}H_{25}$—$(N^+C_5H_5).Cl^-$ are used.

As the amphoteric surfactant, an alkyl carboxybetaine [betaine-based] $C_{12}H_{25}N^+ (CH_3)_2.CH_2COO^-$ is used.

The method of impregnating with a water-soluble material or a thermosoluble material will now be described.

The impregnating water-soluble material or thermosoluble material is charged in a beaker and heated to an appropriate temperature thereby reducing viscosity. A proper amount of a surfactant is added. After reducing the viscosity, a ceramic sintered body is put in the beaker, and the beaker is placed in a vacuum desiccator. The air in the vacuum desiccator is gradually extracted thereby discharging the air in the ceramic sintered body outside of the vacuum desiccator. As the evacuation progresses, air bubbles are formed on a surface of the sintered body, and thus it is found that the air in the sintered body has been extracted. After the completion of extraction of the air, impregnation is conducted by gently returning the air to the desiccator.

The organic material, with which the void part of the present invention is impregnated, is preferably at least one of a thermosetting resin a thermoplastic resin and a resin containing a crosslinking agent.

The resin used for impregnation in the present invention includes a thermosetting resin and a thermoplastic resin. A thermosetting resin or a resin containing a crosslinking agent is preferred. Furthermore, an epoxy resin is preferred.

In the tooth for a dental arch model of the present invention, a method of forming a tooth pulp portion 4 in a dentin portion 2 includes the following steps:
(1) a combustible tooth pulp mold producing step of molding a die having a tooth pulp shape using a combustible material;
(2) a die disposing step of disposing the combustible tooth pulp mold at a predetermined position in a tooth die;
(3) an injection step of injecting an inorganic powder and a binder in the tooth die to obtain a non-sintered injection molding;
(4) a sintering step of sintering the non-sintered injection molding to obtain a sintered body incorporating a space having a tooth pulp shape; and
(5) a tooth pulp producing step of filling a resin, a silicone rubber, a wax or a water-soluble material in the space having a tooth pulp shape in the interior of the sintered body.

The combustible tooth pulp forming step of forming a combustible material tooth pulp formed into a tooth pulp shape using a combustible material is a step of previously forming into a tooth pulp shape using a combustible material upon sintering of a tooth so as to form a tooth pulp shape of the tooth.

Since the tooth formed of an inorganic material is subjected to the sintering step, a space is formed with a material which is combustible during the sintering step and then the space is filled with a material suited for a tooth pulp to complete a tooth. This step is the tooth pulp shape forming step.

The die setting step of setting a combustible tooth pulp mold at a predetermined position in a tooth die is a step of setting a combustible tooth pulp mold in a die. A combustible tooth pulp mold formed previously of a combustible material may be set in a die, or a combustible tooth pulp mold formed continuously in-situ of a combustible material may be set in a die again.

The injecting step of injecting an inorganic powder and a binder into a tooth die to obtain an inject-molded tooth is a step in which an inorganic powder with a dental composition mixed with a binder with heating in a tooth die with a combustible tooth pulp mold formed of a combustible material. In this step, since the combustible tooth pulp mold is thin, injection must be conducted while paying careful attention.

In the present invention, since the tooth is separated into the enamel portion and the dentin portion, only the dentin portion is formed. Also when the tooth is integrally molded by application of the present invention, this step can be applied.

The sintering step of sintering a non-sintered inject molding to obtain a sintered body having a space having a tooth pulp shape therein is a step in which the non-sintered tooth obtained in the injecting step is sintered. The sintering temperature in the sintering step is from 800 to 1,200° C. when a large amount of a glass component is contained. In case of alumina, the sintering temperature is from 1,200 to 1,600° C., and preferably from 1,400 to 1,550° C. At this time, the combustible tooth pulp mold is burned out to form a space having a tooth pulp shape.

The tooth pulp production method of filling the space having a tooth pulp shape in the sintered body with a resin, a silicone rubber, a wax or a water-soluble material is the step of forming a false tooth pulp at the space part of the sintered tooth pulp using a resin, a silicone rubber, a wax or a water-soluble material. Examples of the method include a method of filling using a syringe, and a method of filling a tooth pulp portion of a sintered body with a false tooth pulp material by immersing in the false tooth pulp material and placing in a vacuum vessel, followed by evacuation.

The combustible material may be a material which can be formed into a tooth pulp shape and is not deformed at an injection pressure and an injection temperature upon formation of a tooth and is combustible upon sintering of the tooth to form a space having a tooth pulp shape. The combustible material is specifically a resin, and particularly preferably a thermosetting resin. Specifically, a urea resin, a melamine resin, a phenol resin and an epoxy resin, and crosslinked acryl- and styrene-based resins may be used.

The resin of the tooth pulp portion in a ceramic sintered body of the tooth for a dental arch model of the present invention includes one or more resins including an elastomeric resin, a foamed resin, a thermosetting resin, a thermoplastic resin and a resin containing a crosslinking agent, and is preferably an elastomeric resin or a foamed resin.

The resin of the tooth pulp portion used in the present invention includes a thermosetting resin and a thermoplastic resin. A thermosetting resin or a resin containing a crosslinking agent is preferred. Furthermore, an epoxy resin is preferred.

Specific examples of the thermoplastic resin of the tooth pulp portion used in the present invention include an acryl-based resin, a styrene-based resin, an olefin-based resin, a vinyl chloride-based resin, a urethane-based resin, a polyamide-based resin, a polybutadiene-based resin, a polyacetal-based resin, a saturated polyester-based resin, polycarbonate, polyphenyleneether, a rubber, a vinyl-based resin and polyvinyl acetate. Elastomeric resins and foamed resins such as urethane and rubber are particularly preferred.

The thermosetting resin of the tooth pulp portion used in the present invention includes a urea resin, a melamine resin, a phenol resin and an epoxy resin, and a melamine resin and an epoxy resin are preferred. An epoxy resin is most preferred.

A chemical polymerizable resin is preferred. The reason is that it is easy to impregnate the void part of particles of the sintered body with the resin and to cure the resin.

The chemical polymerizable resin is originally a resin which is polymerized using a chemical catalyst even if it is a resin included in the thermosetting resin or the thermoplastic resin. Particularly preferred resin is a resin which contains a crosslinking agent and has no thermoplasticity.

Any silicone rubber can be used in the tooth pulp portion in the ceramic sintered body of the tooth for a dental arch model of the present invention without any limitation. Examples of the other usable rubber material include a chlorosulfonated polyethylene rubber; a Hypalon rubber, a fluororubber and an isobutene-isoprene rubber; a butyl rubber, a natural rubber and an acrylonitrile-butadiene rubber: a Hiker rubber, a urethane rubber, an ethylene-propylene rubber, a styrene-butadiene rubber and a chloroprene rubber; and neoprene. The rubber hardness (Durometer (JIS K 6253)) is from 10 to 70, and preferably from 20 to 50.

As the wax of the tooth pulp portion in ceramic sintered body of the tooth for a dental arch model of the present invention, for example, animal-derived wax (beeswax, spermaceti, shellac wax, etc.), plant-derived wax (Carnauba wax, Japan tallow, rice bran wax (rice wax), Candelilla wax, etc.), petroleum-derived wax (paraffin wax, microcrystalline wax, etc.), mineral-derived wax (Montan wax, ozocerite, etc.), synthetic wax (Fischer-Tropsch wax, polyethylene wax, fats and oils-based synthetic wax (ester, ketones, amides), and hydrogenated wax can be used. Among these waxes, petroleum-derived wax is preferred and paraffin wax is particularly preferred.

The water-soluble material of the tooth pulp portion in the ceramic sintered body of the tooth for a dental arch model of the present invention contains at least one of polysaccharides and protein-based material. The water-soluble material can exert the effect by pouring water or previously impregnating with water. A protein is preferred.

A hydrophilic polymer is also preferably used as the water-soluble material. For example, cellulose derivatives such as natural product-derived semisynthetic carboxymethyl cellulose (CMC) and methyl cellulose (MC); and synthetic water-soluble polymers such as polyvinyl alcohol (PVA), a polyacryl-based polymer, polyacrylamide (RAM) and polyethylene oxide (PEO) can be used.

Polysaccharides are preferably dextrin, glycogen, cellulose, pectin, konjak mannan and glucomannan, and alginic acid, and more preferably cellulose, pectin, konjak mannan and glucomannan. The reason is that some degree of viscosity is required.

A protein-based compound may be a polymer compound composed mainly of a polypeptide comprising about twenty kinds of L-α-amino acids. In view of the composition, it is preferred to use a simple protein composed only of amino acids, and a conjugated protein comprising nucleic acid, phosphoric acid, a lipid, a saccharide and metal. A starch, gelatin, agar, collagen and elastin are more preferred. Gelatin and agar are still more preferred since it is required to be quickly dissolved in water and to maintain a tooth pulp shape.

In the present invention, although the tooth part is separated into the enamel portion and the dentin portion, only the tooth pulp can be formed of a resin, a silicone rubber, a wax, and a water-soluble material by integral molding of the tooth part through application of the present invention.

In a natural tooth, dental caries tends to result at positions where food residues remain and are mainly generated at an occlusal surface, a space between teeth and a cervix dentis part (boundary between a dental crown and a tooth root). Dental caries easily proceeds on dentin material when compared with enamel material.

Although the dental crown is formed of the enamel texture, it is difficult to completely clean a fissure of the occlusal surface and the dental crown is formed of thin enamel texture, and thus dental caries easily proceeds toward the dentin texture.

In the cervix dentis part, the dentin texture is exposed from the enamel texture and thus dental caries easily proceeds.

In the tooth for a dental arch model of the present invention, a false carious dental portion can be formed between the enamel portion and the dentin portion, or at the periphery thereof, or the dentin side in the vicinity of a transition part of the enamel portion and the dentin portion.

It is preferred that the false carious dental portion is formed in the vicinity of a boundary between the enamel portion and the dentin portion in an occlusal surface or a cervix dentis part. Formation on a dentin portion is particularly preferred compared with an enamel portion.

For example, when the false carious dental portion is formed on the occlusal surface, it is preferred to form a large false carious dental portion at the dentin portion when compared to the enamel portion. In this case, fissure dental caries is reproduced.

When the false carious dental portion is formed at the cervix dentis part, it is preferred to form the false carious dental portion at the dentin side in the vicinity of the transition from the enamel portion to the dentin portion of the tooth surface. In this case, surface dental caries of the tooth root part is reproduced.

The false carious dental portion is formed of an inorganic powder, a resin or a composite. It is preferred that grinding is facilitated in the order of the enamel portion, the dentin portion and the false carious dental portion.

Specific combinations include a combination in which the enamel portion and dentin portion is formed of an inorganic sintered body and the false carious dental portion is formed of a resin or a composite, a combination in which the enamel portion is formed of an inorganic sintered body, the dentin portion is formed of a composite and the false carious dental portion is formed of a resin or a composite which is easily ground when compared with the dentin portion, and a combination in which the enamel portion is formed of a composite, the dentin portion is formed of a composite which is easily ground when compared with the enamel portion and the false carious dental portion is formed of a resin or a composite which is easily ground when compared with dentin.

The inorganic powder, the resin or the composite used as the false carious dental portion can have the same composition as that of the enamel portion or the dentin portion.

The present invention relates to a tooth for a dental arch model which is characterized by containing at least any of a coloring material, fluorescent material and an X-ray contrast material in the false carious dental portion.

It is preferred to add the coloring material to the false carious dental portion. The coloring material may be either a dye or a pigment. The dental caries site can be visually confirmed by coloration and can be easily ground. A deep coloring material is preferred and a black coloring material is particularly preferred.

It is also preferred to use the coloring material in combination with a fluorescent agent or an X-ray contrast medium.

It is preferred to add a fluorescent agent to the false carious dental portion. The fluorescent agent is preferably a UV excitation-type fluorescent agent, and more preferably a UV excitation-type fluorescent pigment. Usually, fluorescence is not emitted upon grinding and it is possible to confirm by emitting fluorescence using black light.

As the fluorescent agent, a fluorescent agent, which is commercially available from a large manufacturer ARBROWN CO., LTD., can be used.

It is possible to use without any limitation substances capable of dispersing in a resin as a base material to emit fluorescence, for example, a fluorescent pigment which is commercially available from SINLOIHI Co., Ltd.

As the UV excitation-type fluorescent agent, a UV excitation-type organic fluorescent pigment or inorganic fluorescent pigment can be used.

It is preferred to impart X-ray contrast properties to the false carious dental portion. X-ray contrast properties can be attained by mixing with X-ray contrast media such as SrO, BaO, ZnO, $ZrO_2$, $La_2O_3$ and other heavy metal element oxides.

Dental caries removal can be confirmed using X-ray photography after treatment training by imparting X-ray contrast properties to the false carious dental portion and is preferred in order to evaluate grinding.

It is preferred to impart X-ray contrast properties to the false carious dental portion. X-ray contrast properties can be attained by mixing with X-ray contrast media such as SrO, BaO, ZnO, $ZrO_2$, $La_2O_3$ and other heavy metal element oxides. The X-ray contrast medium is preferably SrO, BaO, ZnO, $ZrO_2$ or $La_2O_3$, and more preferably ZnO or $ZrO_2$.

The average particle diameter of the coloring material, the fluorescent agent or the X-ray contrast medium is from 0.1 to 30 μm, preferably from 1.0 to 10 μm, and more preferably from 1.0 to 5.0 μm. A coloring material or fluorescent agent may be used, and the X-ray contrast medium may be a dye.

Even when the false carious dental portion has the same composition as that of the enamel portion or the dentin portion, there is no problem if it is possible to decide using the coloring material or the fluorescent agent. Therefore training can be performed by determining a dental caries part based on a color tone.

Even when the false carious dental portion has a different composition from that of the enamel portion or the dentin portion, it is preferred to use a fluorescent agent or X-ray contrast medium as a color, which is almost the same as a dentin color or an enamel color, in order to perform instruction by determining a grinding sensation.

When the false carious dental portion is formed of a material different from that of the dentin portion or the enamel portion, it is possible to perform training of removing the dental caries part by grinding the tooth based on a sensation of different materials by using a fluorescent agent and an X-ray contrast medium in combination in the false carious dental portion. It is possible to confirm later whether or not dental caries is completely removed using black light or X-ray photography.

The false carious dental portion 5 can be reproduced by adhering a dental caries part reproducing material prepared by mixing an inorganic powder, a resin or a composite with at least any one of a coloring material, a fluorescent material and an X-ray contrast material to the enamel portion 1 or the dentin portion 2, or injecting the dental caries part reproducing material in a cavity formed in the enamel portion 1 or the dentin portion 2.

The dental caries part can be reproduced by applying a dental caries part reproducing material containing at least any one of a coloring material, a fluorescent material and an X-ray contrast material to the enamel portion 1 or dentin portion 2, or impregnating with the dental caries part reproducing material. For example, a coloring material, a fluorescent agent and an X-ray contrast medium are dispersed in a solvent and the dentin is impregnated with the resultant dispersion, and thus a false carious dental portion can be formed. This method is preferred since the false carious dental portion can be easily formed.

A method for producing a tooth for a dental arch model of the present invention will be described below.

(When Enamel Portion is Formed of Sintered Body of an Inorganic Powder and Dentin Portion is Formed of Composite)

A sintered body was molded with an $Al_2O_3$ powder (average particle diameter: 0.5 μm) into an enamel portion. A dental caries part reproducing material of a composite (carbon black: 5%, zinc oxide: 10%, UV excitation-type inorganic fluorescent pigment: 30%, epoxy: 55%, a small amount of catalyst) was applied to a part of a dentin side of the sintered body and cured, and then the resultant enamel portion was disposed in a tooth-shaped die and a dentin portion formed of a composite (titanium oxide: 5%, silica powder (5 μm): 70%, epoxy: 25%, a small amount of catalyst) was tamped to obtain a tooth for a dental arch model.

(When Both Enamel Portion and Dentin Portion are Formed of Composite)

A dental caries part reproducing material of a composite (carbon black: 5%, zinc oxide: 10%, UV excitation-type inorganic fluorescent pigment: 30%, epoxy: 55%, a small amount of catalyst) was applied to a part of the dentin side of a molding having an enamel shape formed of a composite (titanium oxide: 5%, silica powder (5 μm): 70%, epoxy: 25%, a small amount of catalyst) and cured, and then the resulting enamel portion was disposed in a tooth-shaped die and a dentin portion formed of a composite (titanium oxide: 5%, silica powder (5 μm: 70%, epoxy: 25%, a small amount of catalyst) was tamped to obtain a tooth for a dental arch model.

The enamel portion and the dentin portion are preferably molded by injection molding.

(When Both Enamel Portion and Dentin Portion are Formed of Sintered Body of an Inorganic Powder)

Sintered bodies were molded with an $Al_2O_3$ powder (average particle diameter: 5 μm) into a dentin portion and an enamel portion. A dental caries part reproducing material of a composite (carbon black: 5%, zinc oxide: 10%, UV excitation-type inorganic fluorescent pigment: 30%, epoxy: 55%, a small amount of catalyst) was applied to a part of the dentin portion which would be inserted into a crown of the enamel portion and cured, and then the enamel portion and the dentin portion were bonded using an epoxy resin to obtain a tooth for a dental arch model.

When the false carious dental portion is formed after the enamel portion and the dentin portion are integrally molded, a tooth is produced in which a void is formed in the false carious dental portion and a hole is provided to the dental caries part and then a dental caries part reproducing material is injected. A small hole may be opened in the thin part from the enamel portion to the dentin portion and the hole used for injection of the dental caries part reproducing material. This thin part is called a fossa in a natural tooth and tends to be a part where dental caries occurs. Thus, a tooth with good reproducibility is preferably obtained. The hole may be preferably made on interproximal surfaces of teeth for the following reason. That is, the resultant tooth is a tooth with good reproducibility since dental caries frequently occurs between adjacent teeth in the front teeth.

In addition to these methods, a lot of combinations thereof can be carried out. Simple combinations are shown below.

Combinations of the enamel portion, the dentin portion and the false carious dental portion are shown in Table 1.

crosslinking agent-containing thermoplastic resin", a thermoplastic resin and a material prepared by impregnation (*) of the dentin portion.

The "material prepared by impregnation (*) of the dentin portion" is used for only the false carious dental portion and is prepared by impregnating the dentin portion with a coloring

TABLE 1

| | Combination Examples | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 12 | 13 | 14 |
| Sintered body of inorganic powder | 1.2.3. | 1.2. | 1.2. | 1.2. | 1.2. | 1 | 1 | 1 | 1 | 1 | 1 | 1 | 1 | 1 |
| Composite | | 3 | | | | 2.3. | 2 | 2 | 2 | | | | | |
| Thermosetting resin | | | 3 | | | | 3 | | | 2.3. | 2 | 2 | | |
| Crosslinking agent-containing thermoplastic resin | | | | | | | | | | | | | | |
| Thermoplastic resin | | | | 3 | | | | 3 | | | 3 | | 2.3 | 2 |
| Dentin portion is impregnated (*) | | | | | 3 | | | | 3 | | | 3 | | 3 |

| | Combination Examples | | | | | | | | | | | | | |
|---|---|---|---|---|---|---|---|---|---|---|---|---|---|---|
| | 15 | 16 | 17 | 18 | 19 | 20 | 21 | 22 | 23 | 24 | 25 | 26 | 27 | 28 |
| Sintered inorganic powder | | | | | | | | | | | | | | |
| Composite | 1.2.3. | 1.2. | 1.2. | 1.2. | 1 | 1 | 1 | 1 | 1 | | | | | |
| Thermosetting resin | | 3 | | | 2.3. | 2 | 2 | | | 1.2.3. | 1.2. | 1.2. | 1 | 1 |
| Crosslinking agent-containing thermoplastic resin | | | | | | | | | | | | | | |
| Thermoplastic resin | | | 3 | | | 3 | | 2.3 | 2 | | 3 | | 2.3 | 2 |
| Dentin portion is impregnated (*) | | | | 3 | | | 3 | | 3 | | | 3 | | 3 |

| Explanation of symbols | |
|---|---|
| Enamel portion | 1 |
| Dentin portions | 2 |
| False carious dental portion | 3 |

(*) The dentin portion is impregnated with a colorant, a UV excitation pigment or an X-ray contrast medium to obtain a false carious dental portion.

The table of combinations is explained below. Each numeral shown in the above table is a numeral shown in the following table. As shown in the following table, "1" denotes an enamel portion, "2" denotes a dentin portion and "3" denotes a false carious dental portion.

In the combination 1, all of the enamel portion, the dentin portion and the false carious dental portion are formed of a sintered body of an inorganic powder. As described above, it is preferred to be soft (easily ground) in the order of the enamel portion, the dentin portion and the false carious dental portion. When the layers are formed of an alumina powder, the sintered body can be easily ground and dental caries can be detected in the grinding process if the enamel portion is formed of particles having a primary particle diameter of 0.1 μm, the tooth dentin portion is formed of particles having a primary particle diameter of 2 μm, and the false carious dental portion is formed of particles having a primary particle diameter of 5 μm.

In the combination 2, the enamel portion and the dentin portion are formed of a sintered body of an inorganic powder. The false carious dental portion is formed of a composite. As described above, it is preferred to become soft in the order of the enamel portion and the dentin portion.

In the combination 3, the false carious dental portion of the combination 2 is formed of a thermosetting resin or a crosslinking agent-containing thermoplastic resin. Both the combination 2 and the combination 3 are preferred combinations.

In the other combinations, similarly, preferred materials used in the enamel portion, the dentin portion and the false carious dental portion can be selected from a sintered body of an inorganic powder, a composite, a "thermosetting resin, a material, a fluorescent material or an X-ray contrast material. This method cannot provide a difference in easiness of grinding with respect to the dentin portion, but when compared with a conventional tooth model, if the tooth is formed of the sintered body of an inorganic powder, it enables grinding training similar to a natural tooth.

It is preferred that the false carious dental portion is softer (easily ground) than the enamel portion and the dentin portion. It is preferred to become soft (easily ground) in the order of the enamel portion, the dentin portion and the false carious dental portion. The reason is that it is possible to perform training for determining dental caries grinding by sensing a grinding material.

The enamel portion is preferably formed of a sintered body of an inorganic powder, a composite or a "thermosetting resin, a crosslinking agent-containing thermoplastic resin", more preferably a sintered body of an inorganic powder or a composite, and still more preferably a sintered body of an inorganic powder. The enamel portion is preferably formed of a hard material having grinding sensation similar to that of the enamel texture.

The dentin portion is preferably formed of a sintered body of an inorganic powder, a composite, a "thermosetting resin, a crosslinking agent-containing thermoplastic resin" or a thermoplastic resin, furthermore sintered body of an inorganic powder, composite, "thermosetting resin, crosslinking agent-containing thermoplastic resin", more preferably a sintered body of an inorganic powder or a composite, and still more preferably a sintered body of an inorganic powder. The reason is that these materials have sensation similar to that of the dentin texture. The thermoplastic resin can be barely used. It often softens upon grinding.

The false carious dental portion may be impregnated with a "thermosetting resin, crosslinking agent-containing thermoplastic resin" or a thermoplastic resin. A "thermosetting resin, a crosslinking agent-containing thermoplastic resin" and a thermoplastic resin are preferred. However, since a grinding sensation does not vary only in response to impregnation, this can not be used in training for different grinding sensations.

EXAMPLES

After forming female dies having tooth shapes of the enamel portion and the dentin portion, dies capable of injection-molding for a desired shape were made. Since shrinkage is caused by degreasing and sintering after molding the enamel portion and the dentin portion, dies were prepared accounting for an excess amount of shrinkage. Injection molding was carried out while adjusting the die for every material.

Production of Tooth for Dental Arch Model According to First Aspect

Example 1

1 kg of alumina pellets for CIM ($Al_2O_3$: 26%, $SiO_2$: 44%, average particle diameter: 0.25 μm, stearic acid: 30%) as a raw material of the enamel portion was injection-molded in a tooth-shaped die to obtain an injection molding.

The resultant injection molding having a shape of the enamel portion was degreased and then sintered (1,300° C., retention time: 10 minutes) to obtain a sintered body 1-1.

1 kg of alumina pellets for CIM ($Al_2O_3$: 26%, $SiO_2$: 44%, average particle diameter: 3.0 μm, stearic acid: 30%) as a raw material of the dentin portion was injection-molded in a tooth-shaped die to obtain an injection molding.

The resultant injection molding having a shape of the dentin portion was degreased and sintered (1,000° C., retention time: 10 minutes) to obtain a sintered body 1-2.

1 kg of alumina pellets for CIM ($Al_2O_3$: 68%, $SiO_2$: 2%, average particle diameter: 0.3 μm, stearic acid: 30%) was injection-molded in a tooth-shaped die to obtain an injection molding.

The resultant injection molding having a shape of the enamel portion was degreased and sintered (1,550° C., retention time: 10 minutes) to obtain a sintered body 2-1.

1 kg of alumina pellets for CIM ($Al_2O_3$: 68%, $SiO_2$: 2%, average particle diameter: 5.0 μm, stearic acid: 30%) as a raw material of the dentin portion was injection-molded in a tooth-shaped die to obtain an injection molding.

The resultant injection molding having a shape of the dentin portion was degreased and sintered (1,400° C., retention time: 15 minutes) to obtain a sintered body 2-2.

A grinding sensation of sintered bodies 1 and 2 obtained by bonding an enamel portion and a dentin portion of the resultant sintered bodies 1-1, 1-2, 2-1 and 2-2 using various adhesives were examined. 30 sintered bodies were produced and tested.

(Epoxy Resin)

An epoxy resin containing a catalyst added therein was applied to the interface between the resultant enamel portion and the dentin portion thereby bonding them. After allowing to standing for 72 hours, a grinding sensation was examined using a diamond bar.

(Ceramic Adhesive)

A ceramic adhesive was applied to the resultant interface between the enamel portion and the dentin portion thereby bonding them. After allowing to standing for 72 hours, a grinding sensation was examined using a diamond bar.

(Cement Material)

A powder-liquid mixing-type cement material capable of curing by reacting an ionic polymer and glass was used. The cement material was applied to the interface between the enamel portion and the dentin portion thereby bonding them. After allowing to standing for 72 hours, the grinding sensation was examined using a diamond bar.

(α-Cyano Acrylate Monomer-Based Adhesive) (Abbreviated Name: α Adhesive)

A commercially available adhesive (Aronalpha®) was applied to the interface between the enamel portion and the dentin portion thereby bonding them. After allowing to standing for 72 hours, a grinding sensation was examined using a diamond bar.

TABLE 2

|  | Adhesion | Grinding sensation | Chipping |
|---|---|---|---|
| Sintered body 1 | | | |
| Epoxy resin | A | A | A |
| Ceramics adhesive | A | A | A |
| Cement material | A | A | B |
| α adhesive | A | A | B |
| Sintered body 2 | | | |
| Epoxy resin | A | A | A |
| Ceramics adhesive | A | A | A |
| Cement material | A | A | B |
| α adhesive | A | A | B |

A: Good results were obtained similar to natural tooth.
B: Although sufficient bonding could be confirmed, chipping partially occurred.

Regarding the sintered body 2, both the dentin portion and the enamel portion showed a grinding sensation similar to that of a natural tooth when compared with the sintered body 1.

Both sintered bodies showed a good grinding sensation. Although chipping occurred in the case of the cement material and a adhesive, a grinding sensation similar to that of a natural tooth was obtained.

Comparative Example 1

After forming female dies having tooth shapes of the enamel portion and the dentin portion, dies capable of a desired shape were made.

In Comparative Example 1, an injection molding die capable of forming a two-layered structure was made so as to obtain a molding comprising a dentin portion and an enamel portion.

1 kg of alumina pellets for CIM ($Al_2O_3$: 26%, $SiO_2$: 44%, average particle diameter: 0.25 μm, stearic acid: 30%) was injection-molded in a tooth-shaped die to obtain an injection molding.

1 kg of alumina pellets for CIM ($Al_2O_3$: 26%, $SiO_2$: 44%, average particle diameter: 3.0 μm, stearic acid: 30%) as a raw material of the dentin portion, in addition to the enamel portion, was injection-molded in a tooth-shaped die to obtain an injection molding.

The resultant injection molding having a shape of the enamel portion was degreased and sintered (1,100° C., retention time: 10 minutes) to obtain a sintered body 3. 30 sintered bodies were produced and tested.

1 kg of alumina pellets for CIM ($Al_2O_3$: 68%, $SiO_2$: 2%, average particle diameter: 0.3 μm, stearic acid: 30%) as a raw material of the enamel portion was injection-molded in a tooth-shaped die to obtain an injection molding.

1 kg of alumina pellets for CIM ($Al_2O_3$: 68%, $SiO_2$: 2%, average particle diameter: 5.0 μm, stearic acid; 30%) as a raw material of the dentin portion, in addition to the enamel portion, was injection-molded in a tooth-shaped die to obtain an injection molding.

The resultant injection molding having a tooth shape was degreased and sintered (1,500° C., retention time: 15 minutes) to obtain a sintered body 4. 30 sintered bodies were produced and tested.

In the sintered bodies 3 and 4, cracking occurred at the boundary between the enamel portion and the dentin portion because of a difference in a shrinkage ratio and therefore bonding was not attained in many samples. During grinding, breakage or chipping occurred.

Example 2

In order to examine the effect on a shrinkage ratio of a sintered body of an amount of a binder during production of pellets, sintered bodies 5 and 6 were produced in the same manner as in Comparative Example 1, except that the amount of stearic acid was changed to 18%.

In the sintered bodies 5 and 6, the enamel portion and the dentin portion were sufficiently bonded and the grinding sensations of both the dentin portion and the enamel portion were similar to that of a natural tooth.

It was found that breakage or chipping, which is caused by a difference in a thermal expansion and shrinkage upon sintering between the dentin portion and the enamel portion, during grinding can be prevented by controlling the amount of the binder during production of pellets.

Example 3

The enamel portion and the dentin portion of the sintered bodies 1-1, 1-2, 2-1, 2-2 produced in the same manner as in Example 1 were bonded using a low-melting point glass powder, and then the grinding sensation was examined.

IP9021 (low-melting point glass, sintering at 575° C.) manufactured by Heraeus K.K. was used as the glass powder to obtain a sintered body 7, while IP9049 (low-melting point glass, sintering at 610° C.) was used to obtain a sintered body 8.

TABLE 3

|  | Adhesion | Grinding sensation | Chipping |
|---|---|---|---|
| Sintered body 7 | C | B | C |
| Sintered body 8 | C | B | C |

A: Good results were obtained similar to a natural tooth.
B: Although sufficient bonding could be confirmed, chipping partially occurred.
C: Excellent when compared with a conventional tooth.

Regarding adhesion, dentin and enamel were bonded to form an integral material. Although a grinding sensation similar to a natural tooth was obtained, cracking at the bonding interface occurred. Although sufficient bonding could be confirmed, chipping partially occurred. It is considered that, since glass as the adhesive did not spread over the entire interface, non-bonded surface is partially formed and thus chipping occurred at the part.

Regarding the sintered bodies 7 and 8, the glass was melted by sintering and the dentin portion and the enamel portion were bonded, and thus cracking occurred at the glass part of the interface upon grinding and peeling or chipping occurred at the adhesive layer of the glass.

Although there remain problems related to adhesion or chipping, in the same manner as Example 1, a remarkable effect was obtained with respect to a grinding sensation.

Example 4

The enamel portion and the dentin portion of the sintered bodies 1-1, 1-2, 2-1 and 2-2 produced in the same manner as in Example 1 were bonded using an epoxy resin, a ceramic adhesive, a cement material and an α adhesive, and then the grinding sensation was examined. In order to control the film thickness, each film thickness of the enamel portion and the dentin portion was limited by mixing alumina powders each having a particle diameter of 700 μm, 400 μm, 350 μm, 250 μm, 150 μm, 50 μm or 20 μm with 3% of each adhesive.

A tooth having a defined adhesive layer was made and ground, and then the adhesive layer was observed by a microscope. It was confirmed that the thickness of the adhesive layer was several tens of microns more than that in the case of the alumina powder used to control the thickness of each adhesive layer.

TABLE 4

| Sintered body 1 |  | Adhesion | Grinding sensation | Chipping |
|---|---|---|---|---|
| Epoxy resin | Alumina powder having particle diameter of 700 μm | B | C | B |
|  | Alumina powder having particle diameter of 400 μm | B | B | B |
|  | Alumina powder having particle diameter of 350 μm | B | B | B |
|  | Alumina powder having particle diameter of 250 μm | B | B | A |
|  | Alumina powder having particle diameter of 150 μm | A | B | A |
|  | Alumina powder having particle diameter of 50 μm | A | A | A |
|  | Alumina powder having particle diameter of 20 μm | A | EX | A |
| Ceramics adhesive | Alumina powder having particle diameter of 700 μm | B | C | B |
|  | Alumina powder having particle diameter of 400 μm | B | B | B |
|  | Alumina powder having particle diameter of 350 μm | B | B | B |
|  | Alumina powder having particle diameter of 250 μm | B | B | A |
|  | Alumina powder having particle diameter of 150 μm | A | B | A |
|  | Alumina powder having particle diameter of 50 μm | A | A | A |
|  | Alumina powder having particle diameter of 20 μm | A | EX | A |
| Cement material | Alumina powder having particle diameter of 700 μm | C | C | C |
|  | Alumina powder having particle diameter of 400 μm | C | B | C |
|  | Alumina powder having particle diameter of 350 μm | C | B | B |
|  | Alumina powder having particle diameter of 250 μm | B | B | B |
|  | Alumina powder having particle diameter of 150 μm | B | B | B |
|  | Alumina powder having particle diameter of 50 μm | A | A | B |
|  | Alumina powder having particle diameter of 20 μm | A | A | B |
| α adhesive | Alumina powder having particle diameter of 700 μm | C | C | C |
|  | Alumina powder having particle diameter of 400 μm | C | B | C |
|  | Alumina powder having particle diameter of 350 μm | C | B | B |
|  | Alumina powder having particle diameter of 250 μm | B | B | B |
|  | Alumina powder having particle diameter of 150 μm | B | B | B |
|  | Alumina powder having particle diameter of 50 μm | A | A | B |
|  | Alumina powder having particle diameter of 20 μm | A | A | B |

TABLE 4-continued

| Sintered body 1 | | Adhesion | Grinding sensation | Chipping |
|---|---|---|---|---|
| Epoxy resin | Alumina powder having particle diameter of 700 μm | B | C | B |
| | Alumina powder having particle diameter of 400 μm | B | B | B |
| | Alumina powder having particle diameter of 350 μm | B | B | B |
| | Alumina powder having particle diameter of 250 μm | B | B | A |
| | Alumina powder having particle diameter of 150 μm | A | A | A |
| | Alumina powder having particle diameter of 50 μm | A | EX | A |
| | Alumina powder having particle diameter of 20 μm | A | EX | A |
| Ceramics adhesive | Alumina powder having particle diameter of 700 μm | B | C | B |
| | Alumina powder having particle diameter of 400 μm | B | B | B |
| | Alumina powder having particle diameter of 350 μm | B | B | B |
| | Alumina powder having particle diameter of 250 μm | B | B | A |
| | Alumina powder having particle diameter of 150 μm | A | A | A |
| | Alumina powder having particle diameter of 50 μm | A | EX | A |
| | Alumina powder having particle diameter of 20 μm | A | EX | A |
| Cement material | Alumina powder having particle diameter of 700 μm | C | C | C |
| | Alumina powder having particle diameter of 400 μm | C | B | C |
| | Alumina powder having particle diameter of 350 μm | C | B | B |
| | Alumina powder having particle diameter of 250 μm | B | B | B |
| | Alumina powder having particle diameter of 150 μm | B | A | B |
| | Alumina powder having particle diameter of 50 μm | A | A | B |
| | Alumina powder having particle diameter of 20 μm | A | A | B |
| α adhesive | Alumina powder having particle diameter of 700 μm | C | C | C |
| | Alumina powder having particle diameter of 400 μm | C | B | C |
| | Alumina powder having particle diameter of 350 μm | C | B | B |
| | Alumina powder having particle diameter of 250 μm | B | B | B |
| | Alumina powder having particle diameter of 150 μm | B | A | B |
| | Alumina powder having particle diameter of 50 μm | A | A | B |
| | Alumina powder having particle diameter of 20 μm | A | A | B |

EX: Good results similar to a natural tooth
A: Good results were obtained similar to a natural tooth.
B: Although sufficient bonding could be confirmed, chipping partially occurred.
C: Excellent when compared with a conventional tooth.

Although it depends on the kind of the adhesive, a particle diameter of the alumina powder greater than 700 μm tends to strengthen a grinding sensation of the adhesive layer during grinding. When the particle diameter is about 500 μm or less, it is considered that the resultant product can be used for grinding training. Furthermore, as the adhesive layer becomes thinner, it becomes impossible to feel a grinding sensation of the adhesive. Although it depends on the kind of the adhesive, when the particle diameter is 500 μm or less, it becomes impossible to feel a grinding sensation of the adhesive. Furthermore, when the particle diameter is 300 μm or less, it is possible to feel that chipping scarcely occurs and adhesion increases. Furthermore, when the particle diameter is 200 μm or less, bonding could be sufficiently performed and a margin part could be ground without feeling discomfort. When the particle diameter is 100 μm or less, a sensation with respect to the bonded layer decreases and transition is possible from the enamel portion to the dentin portion without feeling surprise.

Example 5

700 g of an $Al_2O_3$ powder having a primary particle diameter of 3.0 μm and 300 g (30%) of stearic acid were heat-kneaded and then injected in a dentin-shaped die. The injected molding was degreased at 600° C. for 3 hours and then sintered at 1,400° C. The retention time at the sintering temperature was 15 minutes. As a result of natural air cooling, a dentin portion was completely formed.

700 g of an $Al_2O_3$ powder having a primary particle diameter of 0.3 μm and 300 g (30%) of stearic acid were heat-kneaded and then injected in an enamel-shaped die. The injected molding was degreased at 600° C. for 3 hours and then sintered at 1,500° C. The retention time at the sintering temperature was 15 minutes. As a result of natural air cooling, an enamel portion was completely formed.

The resultant enamel portion and dentin portion were bonded using an epoxy resin. The test results are shown in Table 6. In the test, a dental diamond bar was used.

Examples 6 to 10, Comparative Examples 2 to 6

The same operation as in Example 5 was performed in Examples 6 to 10 and Comparative Examples 2 to 6. Differences from Example 5 are shown in Table 5. The test results are shown in Table 6.

TABLE 5

| | Average particle diameter of alumina (μm) | Amount of alumina (g) | Binder | Amount of binder (g) | Degreasing temperature (° C.) | Molding temperature (° C.) |
|---|---|---|---|---|---|---|
| Enamel | | | | | | |
| Example 5 | 0.3 | 700 | Stearic acid | 300 | 600 | 1500 |
| Example 6 | 0.1 | 700 | Stearic acid | 300 | 600 | 1500 |

TABLE 5-continued

| | Average particle diameter of alumina (μm) | Amount of alumina (g) | Binder | Amount of binder (g) | Degreasing temperature (° C.) | Molding temperature (° C.) |
|---|---|---|---|---|---|---|
| Example 7 | 0.3 | 700 | Stearic acid | 300 | 600 | 1600 |
| Example 8 | 0.8 | 700 | Poly vinyl alcohol | 300 | 600 | 1500 |
| Example 9 | 0.5 | 650 | Stearic acid | 350 | 600 | 1400 |
| Example 10 | 0.5 | 650 | Poly vinyl alcohol | 350 | 600 | 1500 |
| Comparative Example 2 | 0.3 | 700 | Stearic acid | 300 | 600 | 1100 |
| Comparative Example 3 | 0.3 | 700 | Stearic acid | 300 | 600 | 1800 |
| Comparative Example 4 | 5.0 | 700 | Poly vinyl alcohol | 300 | 600 | 1500 |
| Comparative Example 5 | 5.0 | 650 | Stearic acid | 350 | 600 | 1400 |
| Comparative Example 6 | 5.0 | 650 | Poly vinyl alcohol | 350 | 600 | 1800 |
| Dentin | | | | | | |
| Example 5 | 3.0 | 700 | Stearic acid | 300 | 600 | 1400 |
| Example 6 | 2.0 | 700 | Stearic acid | 300 | 600 | 1500 |
| Example 7 | 3.0 | 700 | Stearic acid | 300 | 600 | 1600 |
| Example 8 | 5.0 | 700 | Poly vinyl alcohol | 300 | 600 | 1500 |
| Example 9 | 2.0 | 650 | Stearic acid | 350 | 600 | 1400 |
| Example 10 | 2.0 | 650 | Poly vinyl alcohol | 350 | 600 | 1500 |
| Comparative Example 2 | 3.0 | 700 | Stearic acid | 300 | 600 | 1100 |
| Comparative Example 3 | 3.0 | 700 | Stearic acid | 300 | 600 | 1800 |
| Comparative Example 4 | 0.5 | 700 | Poly vinyl alcohol | 300 | 600 | 1500 |
| Comparative Example 5 | 20.0 | 650 | Stearic acid | 350 | 600 | 1400 |
| Comparative Example 6 | 20.0 | 650 | Poly vinyl alcohol | 350 | 600 | 1800 |

TABLE 6

| | Mold-ability | Grinding properties | Abutment tooth formation properties | Cavity preparation properties | Dentin-enamel transition properties |
|---|---|---|---|---|---|
| Example 5 | A | A | A | A | A |
| Example 6 | A | A | A | A | A |
| Example 7 | A | A | A | A | A |
| Example 8 | A | A | A | A | A |
| Example 9 | A | A | A | A | A |
| Example 10 | A | A | A | A | A |
| Comparative Example 2 | A | C | C | C | C |
| Comparative Example 3 | A | C | C | C | C |
| Comparative Example 4 | A | C | C | C | C |
| Comparative Example 5 | A | C | C | C | C |
| Comparative Example 6 | A | C | C | C | C |

(Grinding sensation, abutment tooth formation properties and cavity preparation properties are evaluated based on similarity with a natural tooth. A: Good, B: Ordinary, C: Poor)

Dentin-enamel transition properties mean a grinding sensation when a grinding material transits the interface between the dentin portion and the enamel portion. It was confirmed whether or not dentin-enamel transition properties are similar to those of a natural tooth.

In Examples 5 to 10, tooth having excellent moldability, grinding sensation, abutment tooth formation properties, and cavity preparation properties and dentin-enamel transition properties could be produced.

In Comparative Example 2, sufficient sintering could not be performed because of a low sintering temperature, resulting in a soft grinding sensation.

In Comparative Example 3, excess sintering was performed because of a high sintering temperature, resulting in a hard grinding sensation. Upon grinding, small chipping (cracking) occurred.

In Comparative Example 4, the enamel portion was soft and the dentin portion became hard. Grinding sensation was very different to that of a natural tooth.

In Comparative Example 5, both the enamel portion and the dentin portion were soft. A grinding sensation was very different from that of a natural tooth.

In Comparative Example 6, both the enamel portion and the dentin portion became harder when compared with Comparative Example 5. A grinding sensation was very different from that of a natural tooth.

Examples 11 to 15, Comparative Examples 7 to 11

Examples and Comparative Examples in which the dentin portion and the enamel portion have the same composition are shown below. A molding method was carried out under the conditions shown in Table 7 in the same manner as in Example 5. As the die, a tooth die was used. The test results are shown in Table 8.

TABLE 7

|  | Primary particle diameter of alumina (μm) | Amount of alumina (g) | Binder | Amount of binder (g) | Degreasing temperature (° C.) | Molding temperature (° C.) |
| --- | --- | --- | --- | --- | --- | --- |
| Example 11 | 0.2 | 700 | Stearic acid | 300 | 600 | 1500 |
| Example 12 | 0.3 | 700 | Stearic acid | 300 | 600 | 1600 |
| Example 13 | 0.5 | 700 | Poly vinyl alcohol | 300 | 600 | 1500 |
| Example 14 | 0.2 | 650 | Stearic acid | 350 | 600 | 1400 |
| Example 15 | 0.2 | 650 | Poly vinyl alcohol | 350 | 600 | 1500 |
| Comparative Example 7 | 0.3 | 700 | Stearic acid | 300 | 600 | 1100 |
| Comparative Example 8 | 0.3 | 700 | Stearic acid | 300 | 600 | 1800 |
| Comparative Example 9 | 5.0 | 700 | Poly vinyl alcohol | 300 | 600 | 1500 |
| Comparative Example 10 | 20.0 | 650 | Stearic acid | 350 | 600 | 1400 |
| Comparative Example 11 | 20.0 | 650 | Poly vinyl alcohol | 350 | 600 | 1800 |

TABLE 8

|  | Moldability | Grinding properties | Abutment tooth formation properties | Cavity preparation properties |
| --- | --- | --- | --- | --- |
| Example 11 | A | A | A | A |
| Example 12 | A | A | A | A |
| Example 13 | A | A | A | A |
| Example 14 | A | A | A | A |
| Example 15 | A | A | A | A |
| Comparative Example 7 | A | C | C | C |
| Comparative Example 8 | A | C | C | C |
| Comparative Example 9 | A | C | C | C |
| Comparative Example 10 | A | C | C | C |
| Comparative Example 11 | A | C | C | C |

(Grinding sensation, abutment tooth formation properties and cavity preparation properties are evaluated based on similarity with a natural tooth. A: Good, B: Ordinary, C: Poor)

In Examples 11 to 15, teeth having excellent moldability, grinding sensation, abutment tooth formation properties and cavity preparation properties could be produced.

Although dentin-enamel transition properties are not observed because of integral molding, the resultant teeth sufficiently endured a practice treatment in the oral cavities.

In Comparative Example 7, sufficient sintering could not be performed because of a low sintering temperature, resulting in a soft grinding sensation.

In Comparative Example 8, excess sintering was performed because of a high sintering temperature, resulting in a hard grinding sensation. Upon grinding, small chipping (cracking) occurred.

In Comparative Example 9, a grinding sensation was very different from that of a natural tooth.

In Comparative Example 10, the tooth became soft when compared with Comparative Example 9. A grinding sensation was very different from that of a natural tooth.

In Comparative Example 11, the tooth was soft when compared with Comparative Example 10. A grinding sensation was very different from that of a natural tooth.

Example 16

After forming female dies having tooth shapes of the enamel portion and the dentin portion, dies capable of injection-molding into a desired shape were made. Since shrinkage is caused by degreasing and sintering after molding the enamel portion and the dentin portion, dies were prepared accounting for an excess amount of shrinkage. Injection molding was carried out while adjusting the die for every material. A shrinkage ratio of enamel was about 10% and that of dentin was about 5%.

(Sintered Body 9)

1 kg of alumina pellets for CIM ($Al_2O_3$: 26%, $SiO_2$: 44%, average particle diameter: 0.25 μm, stearic acid: 30%) as a raw material of the enamel portion was injection-molded in a tooth-shaped die to obtain an injection molding 7-1.

1 kg of alumina pellets for CIM ($Al_2O_3$: 26%, $SiO_2$: 44%, average particle diameter: 3.0 μm, stearic acid: 30%) as a raw material of the dentin portion was injection-molded in a tooth-shaped die to obtain an injection molding 7-2.

The resultant injection moldings were degreased and sintered (1,200° C., the retention time: 10 minutes) in the presence of the following glass powder interposed between the dentin portion and the enamel portion to obtain a sintered body 9.

(Sintered Body 10)

1 kg of alumina pellets for CIM ($Al_2O_3$: 100%, average particle diameter: 0.3 μm, stearic acid: 30%) as a raw material of the enamel portion was injection-molded in a tooth-shaped die to obtain an injection molding 8-1.

1 kg of alumina pellets for CIM ($Al_2O_3$: 68%, $SiO_2$: 2%, average particle diameter: 5.0 μm, stearic acid: 30%) as a raw material of the dentin portion was injection-molded in a tooth-shaped die to obtain an injection molding 8-2.

The resultant injection moldings were degreased and sintered (1,400° C., the retention time: 15 minutes) in the presence of the following glass powder interposed between the dentin portion and the enamel portion to obtain a sintered body 10.

As the glass powder, fused silica having an average particle diameter of 0.5 μm and a maximum particle diameter of 2.0 μm was used.

(Sintered Bodies 11, 12)

The enamel portion and the dentin portion of the sintered bodies 9-1, 9-2, 10-1 and 10-2 obtained in the same manner as above were sintered in the presence of a quartz glass powder interposed between the dentin portion and the enamel portion to obtain sintered bodies 11 and 12.

The sintered bodies 9 to 12 were evaluated by a grinding test and a bonding state test.

In the grinding test, it could be confirmed that all sintered bodies 9 to 12 had a good grinding sensation.

In the bonding state test, each of the sintered bodies 9 to 12 was sliced into a thickness of about 5 mm using a diamond disk and then the bonding state was confirmed. It could be confirmed that all sintered bodies 9 to 12 were in a good bonding state.

Production of Tooth for Dental Arch Model of Second Aspect

Example 17

700 g of an $Al_2O_3$ powder having a primary particle diameter of 0.3 μm and 300 g (30%) of stearic acid were heat-kneaded and then injected in an enamel-shaped die. The injected molding was degreased at 600° C. for 3 hours and then sintered at 1500° C. The retention time at the sintering temperature was 15 minutes. As a result of natural air cooling, an enamel portion was completely formed.

The resultant enamel portion was placed in a tooth-shaped die and an epoxy resin was injected in the remaining dentin portion. The test results are shown in Table. In the test, a dental diamond bar was used.

Examples 18 to 22, Comparative Examples 12 to 16

The same operation as in Example 17 was performed in Examples 18 to 22 and Comparative Examples 12 to 16. Differences from Example 17 are shown in Table 9. The test results are shown in Table 10.

TABLE 9

| Enamel | Primary particle diameter of alumina (μm) | Amount of alumina (g) | Binder | Amount of binder (g) | Degreasing temperature (° C.) | Molding temperature (° C.) |
| --- | --- | --- | --- | --- | --- | --- |
| Example 17 | 0.3 | 700 | Stearic acid | 300 | 600 | 1500 |
| Example 18 | 0.2 | 700 | Stearic acid | 300 | 600 | 1500 |
| Example 19 | 0.3 | 700 | Stearic acid | 300 | 600 | 1600 |
| Example 20 | 0.5 | 700 | Poly vinyl alcohol | 300 | 600 | 1500 |
| Example 21 | 0.2 | 650 | Stearic acid | 350 | 600 | 1400 |
| Example 22 | 0.2 | 650 | Poly vinyl alcohol | 350 | | 1500 |
| Comparative Example 12 | 0.3 | 700 | Stearic acid | 300 | 600 | 1100 |
| Comparative Example 13 | 0.3 | 700 | Stearic acid | 300 | 600 | 1800 |
| Comparative Example 14 | 5.0 | 700 | Poly vinyl alcohol | 300 | 600 | 1500 |
| Comparative Example 15 | 20.0 | 650 | Stearic acid | 350 | 600 | 1400 |
| Comparative Example 16 | 20.0 | 650 | Poly vinyl alcohol | 350 | 600 | 1800 |

TABLE 10

|  | Mold-ability | Grinding properties | Abutment tooth formation properties | Cavity preparation properties | Dentin-enamel transition properties |
|---|---|---|---|---|---|
| Example 17 | A | A | A | A | A |
| Example 18 | A | A | A | A | A |
| Example 19 | A | A | A | A | A |
| Example 20 | A | A | A | A | A |
| Example 21 | A | A | A | A | A |
| Example 22 | A | A | A | A | A |
| Comparative Example 12 | A | C | C | C | C |
| Comparative Example 13 | A | C | C | C | C |
| Comparative Example 14 | A | C | C | C | C |
| Comparative Example 15 | A | C | C | C | C |
| Comparative Example 16 | A | C | C | C | C |

(Grinding sensation, abutment tooth formation properties and cavity preparation properties are evaluated based on similarity with a natural tooth. A: Good, B: Ordinary, C: Poor)

Each evaluation was confirmed whether or not abutment tooth formation and cavity molding show a grinding sensation similar to that of a natural tooth in grinding of a tooth model. It was evaluated by the fact that grinding sensation varies between the enamel texture and the dentin texture, like a natural tooth, or evaluated whether or not a grinding sensation upon molding is similar to that of a natural tooth.
A: similar to a natural tooth
C: too hard or soft by far when compared with a natural tooth, use sensation similar to a commercially available resin tooth
B: middle between A and C Dentin-enamel transition properties were evaluated by confirming whether or not a grinding sensation is similar to those of a natural tooth when a grinding material transits the interface between the dentin portion and the enamel portion.

In Examples 17 to 22, tooth having excellent moldability, grinding sensation, abutment tooth formation properties, and cavity preparation properties and dentin-enamel transition properties could be produced.

In Comparative Example 12, sufficient sintering could not be performed because of a low sintering temperature, resulting in a soft grinding sensation.

In Comparative Example 13, excess sintering was performed because of a high sintering temperature, resulting in a hard grinding sensation. Upon grinding, small chipping (cracking) occurred.

In Comparative Example 14, the enamel portion became hard. A grinding sensation was very different from that of a natural tooth.

In Comparative Example 15, the enamel became soft. A grinding sensation was very different from that of a natural tooth.

In Comparative Example 16, both the enamel portion became harder when compared with Comparative Example 15. A grinding sensation was very different from that of a natural tooth.

Examples 23 to 27, Comparative Examples 17 to 21

Examples and Comparative Examples in which the dentin portions have the same composition as in Examples 18 to 22 and Comparative Examples 12 to 16 and a composite obtained by mixing 75% of an alumina powder and 25% of an epoxy resin was used as the dentin portions are shown below.

A molding method was carried out in the same manner as in Example 17. As the die, a tooth die was used. The test results are shown in Table 11.

TABLE 11

|  | Mold-ability | Grinding properties | Abutment tooth formation properties | Cavity preparation properties |
|---|---|---|---|---|
| Example 23 | A | A | A | A |
| Example 24 | A | A | A | A |
| Example 25 | A | A | A | A |
| Example 26 | A | A | A | A |
| Example 27 | A | A | A | A |
| Comparative Example 17 | A | C | C | C |
| Comparative Example 18 | A | C | C | C |
| Comparative Example 19 | A | C | C | C |
| Comparative Example 20 | A | C | C | C |
| Comparative Example 21 | A | C | C | C |

(Grinding sensation, abutment tooth formation properties and cavity preparation properties are evaluated based on similarity with a natural tooth. A: Good, B: Ordinary, C: Poor)

In Examples 23 to 27, teeth having excellent moldability, grinding sensation, abutment tooth formation properties and cavity preparation properties could be produced.

Although dentin-enamel transition properties are not observed because of integral molding, the resultant teeth sufficiently endured a practice treatment in the oral cavities. The grinding sensation of dentin was improved when compared with Examples 17 to 22.

In Comparative Example 17, sufficient sintering could not be performed because of a low sintering temperature, resulting in a soft grinding sensation.

In Comparative Example 18, excess sintering was performed because of a high sintering temperature, resulting in a hard grinding sensation. Upon grinding, small chipping (cracking) occurred.

In Comparative Example 19, the enamel portion became soft. A grinding sensation was very different from that of a natural tooth.

In Comparative Example 20, the enamel portion became soft. A grinding sensation was very different from that of a natural tooth.

In Comparative Example 21, the enamel portion became soft when compared with Comparative Example 20. A grinding sensation was very different from that of a natural tooth.

Example 28

An embodiment was produced in the same manner as described above, except that the enamel portion had the same composition as in Example 17 and a composite was used as the dentin portion.

The composite was prepared by mixing 55% of an alumina powder, 20% of zinc oxide and 25% of an epoxy resin. The molding method of the enamel portion was carried out in the same manner as in Example 1. As the die, a tooth die was used. Cavity preparation was performed as a test and a photograph of the resultant tooth model was taken by dental X-ray equipment. As a result, a photograph of a dentin shape could be easily taken.

Example 29

An embodiment was produced in the same manner as described above, except that the enamel portion had the same composition as in Example 17 and cement was used as the dentin portion.

The cement was prepared by mixing 2.6 g of a powder comprising 93.5% of aluminosilicate glass and 6.5% of tartaric acid with 1.0 g of a liquid comprising 45% of polyacrylic acid and 55% of tricarboxylic acid. The molding method of the enamel portion was carried out in the same manner as in Example 1. As the die, a tooth die was used. Cavity preparation was performed as a test and a photograph of the resultant tooth model was taken by dental X-ray equipment. As a result, a photograph of a dentin shape could be easily taken.

Example 30

500 g of a zirconia ($ZrO_2$) powder having a primary particle diameter of 3.0 μm, 200 g of a silica ($SiO_2$) powder and 300 g (30%) of stearic acid were heat-kneaded and then injected in an enamel-shaped die. The resultant injected molding was degreased at 600° C. for 3 hours and then sintered at 1,300° C. The retention time at the sintering temperature was 2 hours. As a result of natural air cooling, an enamel portion was completely formed. In the same manner as in Example 17, a tooth was produced.

When compared with a tooth containing alumina as a main component, the resultant tooth included a part having a poor grinding sensation. However, when compared with an enamel tooth formed of a resin or a composite, the tooth was almost not at all ground excessively and was not soft, and also showed a grinding sensation similar to that of a natural tooth. When compared with the glass, the tooth did not cause chipping and showed grinding sensation similar to that of a natural tooth. The transition part to the dentin portion showed a transition sensation from an enamel texture to a dentin texture, which had never been achieved by a conventional tooth model, and practice treatments could be performed without using a natural tooth.

Impartation of Toughness to Sintered Body of Inorganic Powder

Examples 31 to 49, Comparative Examples 22 to 25

Production of Sintered Tooth

A die capable of injecting molding into a tooth shape was made. 1 kg of alumina pellets for CIM ($Al_2O_3$: 26%, $SiO_2$: 44%, average particle diameter: 3.0 μm, stearic acid: 30%) as a raw material of the tooth was injection-molded in a tooth-shaped die to obtain an injection molding.

The resultant injection molding having a shape of the tooth part was degreased and then sintered (1,300° C., retention time: 10 minutes) to obtain a sintered body 13.
(Production of Sintered Body of Enamel Portion and Dentin Portion)

Dies capable of injecting molding for shapes of the enamel portion and the dentin portions of the tooth were made. Since shrinkage is caused by degreasing and sintering after molding the enamel portion and the dentin portion, dies were prepared accounting for an excess amount of shrinkage. Injection molding was carried out while adjusting the die for every material.

1 kg of alumina pellets for CIM ($Al_2O_3$: 68%, $SiO_2$: 2%, average particle diameter: 0.3 μm, stearic acid: 30%) as a raw material of the enamel portion was injection-molded in a tooth-shaped die to obtain an injection molding.

The resultant injection molding having a shape of the enamel portion was degreased and then sintered (1,550° C., retention time: 10 minutes) to obtain a sintered body 14-1.

1 kg of alumina pellets for CIM ($Al_2O_3$: 68%, $SiO_2$: 2%, average particle diameter: 5.0 μm, stearic acid: 30%) as a raw material of the dentin portion was injection-molded in a tooth-shaped die to obtain an injection molding.

The resultant injection molding having a shape of the enamel portion was degreased and then sintered (1,400° C., retention time: 15 minutes) to obtain a sintered body 14-2.
(Impregnation)

The resulting sintered bodies 13, 14-1 and 14-2 were embedded in each impregnation material and placed in a vacuum vessel, followed by evacuation. It was confirmed that the void part of the sintered bodies were sufficiently impregnated with the impregnation material. The sintered bodies 14-1 and 14-2 were bonded using an epoxy resin adhesive.

A grinding sensation of the resultant teeth was confirmed. 30 sintered bodies were produced and tested.
(Tested Impregnation Material)
Paraffin wax (Nippon Seiro Co., Ltd., standard paraffin wax): Paraffin wax was sufficiently heated before embedding the sintered body. It was confirmed that the paraffin wax was liquefied.
Beeswax (unbleached beeswax): Beeswax was sufficiently heated before embedding the sintered body. It was confirmed that the beeswax wax was liquefied.
Cellulose (manufactured by Shin-Etsu Chemical Co., Ltd., SM-8000): A silicon resin containing a catalyst added therein was used. After allowing to standing for 72 hours, a grinding sensation was examined using a diamond bar.
Konjak mannan (Ina Food Industry Co., Ltd.): Konjak mannan was dissolved in hot water so as to obtain suitable hardness and then heated. Before placing in a desiccator, a coagulating agent was introduced.
Agar (Ina Food Industry Co., Ltd.): Agar was dissolved in hot water so as to obtain suitable hardness and then heated.
Gelatin (Nitta Gelatin Inc.): Gelatin was dissolved in hot water so as to obtain suitable hardness and then heated.
Epoxy resin (Low-viscosity epoxy resin Z-2/H-07): An epoxy resin containing a catalyst added therein was used. After allowing to standing for 72 hours, a grinding sensation was examined using a diamond bar.
Acryl resin (manufactured by KURARAY CO., LTD., MMA monomer): An acryl resin containing a chemical polymerization catalyst added therein was used. After allowing to standing for 72 hours, a grinding sensation was examined using a diamond bar.
Silicone resin (RTV silicone resin M8017: Asahi Kasei Corporation): A silicone resin containing a catalyst added therein was used. After allowing to standing for 72 hours, a grinding sensation was examined using a diamond bar.

In Comparative Examples 22 to 25, non-impregnated sintered bodies were used.

In the test, grinding was performed using a diamond grinding material (using an air turbine) rotating at a high speed of 400,000 rpm. Regarding Examples 31, 32, 37 and 38, the test was performed without water pouring. Regarding other Examples and Comparative Examples, the test was performed while water pouring.

TABLE 12

| | Impregnation material | Grinding sensation | Chipping | Grinding toughness | Biologic wet sensation |
|---|---|---|---|---|---|
| Sintered body 13 | | | | | |
| Example 31 | Paraffin wax | B | A | A | B |
| Example 32 | Beeswax | B | A | A | B |
| Example 33 | Cellulose | B | A | C | C |
| Example 34 | Konjak mannan | B | A | B | A |
| Example 35 | Agar | B | A | B | A |
| Example 36 | Gelatin | B | A | B | A |

TABLE 12-continued

| | Impregnation material | Grinding sensation | Chipping | Grinding toughness | Biologic wet sensation |
|---|---|---|---|---|---|
| Comparative Example 22 Sintered body 14 | | B | A | D | D |
| Example 37 | Paraffin wax | A | A | A | B |
| Example 38 | Beeswax | A | A | A | B |
| Example 39 | Cellulose | A | A | C | C |
| Example 40 | Konjak mannan | A | A | B | A |
| Example 41 | Agar | A | A | B | A |
| Example 42 | Gelatin | A | A | B | A |
| Comparative Example 23 | | A | A | D | D |

A: Good results similar to a natural tooth
B (Grinding sensation): It was impossible to sufficiently express dentin and enamel. Although the enamel portion was soft, toughness was similar to that of a natural tooth.
B (Grinding toughness): There was slight elastic sensation, not toughness.
C (Grinding toughness): Toughness was soft when compared with a natural tooth.
A (Biologic wet sensation): Similar to a natural tooth, biologic wet sensation and wet sensation with carnosity were attained. Good results were obtained.
B (Biologic wet sensation): Similar to a natural tooth, biologic wet sensation was attained and carnosity sensation was slightly inferior when compared with A.
C (Biologic wet sensation): When compared with a natural tooth, biologic wet sensation was different.
D: Toughness upon grinding was not attained, and dust was severely scattered.

Examples 31, 32, 37 and 38 showed toughness when compared with Comparative Examples 22 and 23, and a grinding sensation similar to that of a natural tooth was obtained. Sensation of a body fluid from a dentinal tubule was also similar. The amount of grind dust was smaller than that in case of Comparative Example 22, and grind dust was scarcely scattered. Without water pouring, grinding could be easily performed. It was confirmed that training of tooth grinding could be easily performed without water pouring. Similar to a natural tooth, although biologic wet sensation was confirmed, wax melting was slightly different from the case of the living body.

Regarding Examples 33 and 39, toughness was confirmed when compared with Comparative Examples 22 and 23, and a grinding sensation similar to that of a natural tooth was obtained.

Although dissolution of cellulose caused by water pouring was observed, the test was finished without causing any problem. The amount of grind dust was smaller than the case of Comparative Example 22, grind dust was scarcely scattered. However, biologic wet sensation was different.

Regarding Examples 34, 35, 36, 40, 41 and 42, toughness was confirmed when compared with Examples 33 and 39, and a grinding sensation similar to that of a natural tooth was obtained. Sensation of a body fluid from a dentinal tubule was also similar. The amount of grind dust was smaller than that in case of Comparative Example 22, and grind dust was scarcely scattered. Without water pouring, grinding could be easily performed.

It was confirmed that training of tooth grinding can be easily performed in an actual clinical environment under water pouring. Similar to a natural tooth, biologic wet sensation was confirmed and good results were obtained.

Example 43

The sintered bodies 13 and 14 were embedded in Fett (beef tallow) as the impregnation material to obtain a tooth. Fett was sufficiently heated before embedding the sintered body and it was confirmed that Fett was liquefied. After cooling for 24 hours and as a result of grinding, the tooth displayed an excellent grinding sensation, grinding toughness and wet sensation similar to the living body. Particularly, a wet sensation similar to the living body was excellent when compared with other materials. Slipperiness upon grinding and odor generated upon excess grinding were also similar.

TABLE 13

| | Impregnation material | Grinding sensation | Chipping | Grinding toughness | Biologic wet sensation |
|---|---|---|---|---|---|
| Sintered body 13 | | | | | |
| Example 44 | Epoxy resin | B | A | A | A |
| Example 45 | Acryl resin | B | A | A | A |
| Example 46 | Silicone resin | B | A | B | B |
| Comparative Example 24 | | B | A | D | D |
| Sintered body 14 | | | | | |
| Example 47 | Epoxy resin | A | A | A | A |
| Example 48 | Acryl resin | A | A | A | A |
| Example 49 | Silicone resin | A | A | B | B |
| Comparative Example 25 | | A | A | D | D |

A: Good results similar to a natural tooth
B (Grinding sensation): It was impossible to sufficiently express dentin and enamel.
B (Grinding toughness): There was slight elastic sensation, not toughness.
D: Toughness upon grinding was not confirmed and large dust
A (Crushing sensation upon grinding): Crushing sensation upon grinding was scarcely confirmed and sensation of grinding the living tooth was confirmed.
B (Crushing sensation upon grinding): Crushing sensation upon grinding was confirmed and slightly different sensation of grinding living tooth was confirmed.
D: Toughness upon grinding was confirmed and large dust scatter.

Regarding Examples 44 and 45, toughness was confirmed when compared with Comparative Example 24 and grinding sensation similar to that of a natural tooth was obtained. The amount of grind dust was smaller than in Comparative Example 24 and grind dust was scarcely scattered. A crushing sensation peculiar to ceramics upon grinding was scarcely confirmed and similar sensation of grinding the living tooth was obtained.

Regarding Example 46, toughness was confirmed when compared with Comparative Example 24 and a grinding sensation similar to that of a natural tooth was obtained. The amount of grind dust was smaller than that in Comparative Example 24 and grind dust was scarcely scattered. When compared with Examples 44 and 45, the amount of grind dust scattered was large. The grinding sensation is similar to that of a natural tooth. When compared with Examples 44 and 45, it is considered that sensation of resistance upon grinding of a natural tooth is slightly inferior. Although it is inferior to Examples 44 and 45, a state of a natural tooth could be reproduced.

Regarding Example 47 and 48, toughness was confirmed when compared with Comparative Example 25 and a grinding sensation similar to that of a natural tooth was obtained. The amount of grind dust was smaller when compared with Comparative Example 25 and grind dust was scarcely scattered. Upon transition from the enamel portion to the dentin portion, a tough grinding sensation similar to that of a natural tooth was obtained. Crushing sensation peculiar to ceramics upon grinding was scarcely confirmed and sensation was similar to sensation of grinding the living tooth.

Regarding Example 49, toughness was confirmed when compared with Comparative Example 25 and a grinding sensation similar to that of a natural tooth was obtained. The amount of grind dust was smaller when compared with Comparative Example 25 and grind dust was scarcely scattered. When compared with Examples 47 and 48, the amount of grind dust scattered was larger. A grinding sensation is also similar to that of a natural tooth.

Upon transition from the enamel portion to the dentin portion, a tough grinding sensation similar to that of a natural tooth was obtained. When compared with Examples 47 and 48, it is considered that the sensation of resistance which is different from a natural tooth was slightly inferior. Although it was inferior to Examples 47 and 48, a state of a natural tooth could be reproduced.

Formation of Tooth Pulp Portion

Examples 50 to 55

Production of Combustible Tooth Pulp Mold

A wax having a tooth pulp shape of the objective tooth was modeled using a silicone rubber and an epoxy resin was poured into the silicone rubber to obtain a combustible tooth pulp mold.

(Production of Sintered Body of Tooth)

A die capable of injection molding into the objective shape of a tooth shape was made. In this die, a stopper part was provided so as to dispose a combustible tooth pulp mold. 1 kg of alumina pellets for CIM ($Al_2O_3$: 26%, $SiO_2$: 44%, average particle diameter 0.3 μm, stearic acid: 30%) as a raw material of the tooth was injection-molded in a tooth-shaped die in which a combustible tooth pulp mold was disposed to obtain an injection molding.

The resultant injection molding having a shape of the tooth part was degreased and then sintered (1,300° C., retention time: 10 minutes) to obtain a sintered body 15.

(Production of Sintered Bodies of Enamel Portion and Dentin Portion)

A die capable of injection molding into the objective shape of a tooth shape was made. In this die, a stopper part was provided so as to dispose a combustible tooth pulp mold. Since shrinkage is caused by degreasing and sintering after molding the enamel portion and the dentin portion, dies were prepared accounting for an excess amount of shrinkage. Injection molding was carried out while adjusting the die for every material.

1 kg of alumina pellets for CIM ($Al_2O_3$: 68%, $SiO_2$: 2%, average particle diameter 0.3 μm, stearic acid: 30%) as a raw material of the enamel portion was injection-molded in a tooth-shaped die to obtain an injection molding.

The resultant injection molding having a shape of the enamel portion was degreased and then sintered (1,550° C., retention time: 10 minutes) to obtain a sintered body 16-1.

1 kg of alumina pellets for CIM ($Al_2O$: 68%, $SiO_2$: 2%, average particle diameter 5.0 μm, stearic acid: 30%) as a raw material of the dentin portion was injection-molded in a tooth-shaped die in which a combustible tooth pulp mold was disposed to obtain an injection molding.

The resultant injection molding having a shape of the dentin portion was degreased and sintered (1,400° C., retention time: 15 minutes) to obtain a sintered body 16-2. The sintered bodies 16-1 and 16-2 were bonded using a resinous adhesive to obtain a sintered body 16.

(Injection of Tooth Pulp Material)

In spaces for tooth pulps of the resultant sintered bodies 15 and 16, each material was injected using a syringe.

A grinding sensation of the resultant tooth was examined. 30 sintered bodies were produced and tested.

(Tested Resin)

Polyvinyl alcohol: Polyvinyl alcohol was filled and then dried. After allowing to standing for 72 hours, a grinding sensation was examined using a diamond bar.

Urethane rubber having hardness of 30: A urethane rubber containing chemical polymerization catalyst added therein was used. After allowing to standing for 72 hours, grinding sensation was examined using a diamond bar. Silicone rubber (RTV silicone rubber resin M8017: Asahi Kasei Corporation): A silicone rubber resin containing a catalyst added therein was used. After allowing to standing for 72 hours, grinding sensation was examined using a diamond bar.

Comparative Examples 26 to 31

Using, as Comparative Examples, those wherein an enamel/dentin portion was formed of epoxy (Comparative Examples 26 to 28) and those wherein the enamel/dentin portion was formed of a melamine resin (Comparative Examples 29 to 31), the same resin as in Examples was injected into the tooth pulp portion.

(Test Method)

Ten dentists were asked to evaluate test items of samples of Examples 50 to 55 and Comparative Examples 26 to 31. Three test pieces were ground for each sample. In the following Table 14, most frequent evaluation results are shown.

Dental pulp exposure sensation means grinding sensation when reached the pulp portion after grinding to the enamel and dentin portions from the occlusal surface for a treatment of the tooth pulp.

Root canal cleaning means a cleaning process performed by scraping out the pulp in the root canal using a thin grinding tool referred to a reamer inserted into the root canal. It shows evaluation results of cleaning properties.

Root canal extension means an extension of the inside of the cleaned root canal so as to facilitate filling of root canal filler. It shows evaluation results of expansion properties.

TABLE 14

| | Filling material | Dental pulp exposure sensation | Root canal cleaning | Root canal extension |
|---|---|---|---|---|
| Sintered body 15 | | | | |
| Example 50 | Polyvinyl alcohol | B | B | B |
| Example 51 | Urethane rubber | A | A | A |
| Example 52 | Silicone rubber | A | A | A |
| Sintered body 16 | | | | |
| Example 53 | Polyvinyl alcohol | B | B | B |
| Example 54 | Urethane rubber | A | A | A |
| Example 55 | Silicone rubber | A | A | A |
| Comparative Example 26 | Polyvinyl alcohol | D | C | C |
| Comparative Example 27 | Urethane rubber | D | C | C |
| Comparative Example 28 | Silicone rubber | D | C | C |
| Comparative Example 29 | Polyvinyl alcohol | D | C | C |
| Comparative Example 30 | Urethane rubber | D | C | C |
| Comparative Example 31 | Silicone rubber | D | C | C |

A: Good results similar to a natural tooth
B: Grinding sensation of dentin was different from that of pulp and it was impossible to sufficiently express, however, it sufficiently endured training.
C: Grinding sensation of the interface between dentin and pulp was different from that of a natural tooth.
D: Grinding sensation of tooth was quite different and toughness upon dental pulp exposure was not confirmed, and sensation upon root canal cleaning and root canal extension was different.

Regarding Examples 50 and 53, it was possible to experience good dental pulp exposure and, although slight hard root canal cleaning was confirmed, it was possible to sufficiently experience a treatment of a root canal. Toughness of the pulp was confirmed and there were respects which were excellent when compared with Examples 51, 52, 54 and 55.

Regarding Examples 51, 52, 54 and 55, it was possible to experience good dental pulp exposure when compared with Examples 50 and 53, and it was possible to sufficiently experience a root canal treatment, such as root canal cleaning or root canal extension. Sensation of the interface between pulp and dentin was similar. Sensation of removal of the pulp upon root canal cleaning was similar.

Regarding Comparative Examples 26 and 28, a state of the interface between dentin of epoxy or a melamine resin, and polyvinyl alcohol, a urethane rubber or a silicone rubber, and thus a grinding sensation similar to that of a natural tooth could not be reproduced. Regarding dental pulp exposure sensation, sensation upon dental pulp exposure was largely different. In the root canal cleaning, sensation was different from that of a natural tooth because of rubbing with epoxy or a melamine resin. In root canal extension, sensation of extending by grinding dentin was largely different.

Formation of False Carious Dental Portion

Example 56

700 g of an $Al_2O_3$ powder having a primary particle diameter of 0.3 μm and 300 g (30%) of stearic acid were heat-kneaded and then injected in an enamel-shaped die. The resultant injected molding was degreased at 600° C. for 3 hours and then sintered at 1500° C. The retention time at the sintering temperature was 15 minutes. As a result of natural air cooling, an enamel portion was completely formed. A small amount of an epoxy resin prepared by mixing 10% of a UV excitation-type inorganic fluorescent pigment with 0.2% of carbon black was applied to the part to be contacted with the dentin portion having an enamel to obtain a false carious dental portion.

Next, the enamel portion was placed in a tooth-shaped die and an epoxy resin having an ivory color was injected in the remaining dentin portion. In the test, a dental diamond bar was used.

Examples 57 to 61

The same operation as in Example 56 was performed in Examples 57 to 61. Points different from Example 56 are shown in Table 15.

Grinding sensation, abutment tooth formation properties and cavity preparation properties were evaluated by similarity with a natural tooth. Good results were obtained. Particularly dentin-enamel transition properties were excellent as a result of a confirmation whether or not a grinding sensation is similar to those of a natural tooth when a grinding material transits the interface between the dentin layer and the enamel layer.

The black part was removed at the dental caries part and it could be confirmed whether or not the dental caries part can be actually removed, using black light.

Examples 62 to 67

Using composites in which the enamel portions are formed of alumina powder sintered bodies of Examples 56 to 61 and the dentin portions were formed of a composition prepared by mixing 75% of an alumina powder with 25% of an epoxy resin, a small amount of an epoxy resin containing 10% of a UV excitation-type inorganic fluorescent pigment added therein was applied to a region where the false carious dental portion was contacted with dentin of the enamel-shaped part to obtain a false carious dental portion. Both the false carious dental portion and the dentin portion were colored ivory.

The molding, method was carried out in the same manner as in Example 56. As the die, a tooth die was used.

Grinding sensation, abutment tooth formation properties and cavity preparation properties were evaluated based on similarity with a natural tooth. Good results were obtained. Particularly dentin-enamel transition properties were excellent as a result of a confirmation whether or not a grinding sensation is similar to that of a natural tooth when a grinding material transits the interface between the dentin layer and the enamel layer.

The grinding sensation of the dental caries portion was different and it could be confirmed whether or not the dental caries portion can be actually removed, using black light. An expert could easily feel sensation of the dental caries part, whereas, a beginner could ground the dental caries portion as he repeats training.

Thus, it was confirmed that it was easy to experience grinding of the dental caries portion.

Example 68

A tooth in which the enamel portion and the dentin portion have the same composition as in Example 62 and a composition prepared by mixing 20% of zinc oxide with 80% of an epoxy resin was used as the false carious dental portion was produced. The molding method was carried out in the same

TABLE 15

| Enamel | Primary particle diameter of alumina (μm) | Amount of alumina (g) | Binder | Amount of binder (g) | Degreasing temperature (° C.) | Molding temperature (° C.) |
|---|---|---|---|---|---|---|
| Example 56 | 0.3 | 700 | Stearic acid | 300 | 600 | 1500 |
| Example 57 | 0.2 | 700 | Stearic acid | 300 | 600 | 1500 |
| Example 58 | 0.3 | 700 | Stearic acid | 300 | 600 | 1600 |
| Example 59 | 0.5 | 700 | Poly vinyl alcohol | 300 | 600 | 1500 |
| Example 60 | 0.2 | 650 | Stearic acid | 350 | 600 | 1400 |
| Example 61 | 0.2 | 650 | Poly vinyl alcohol | 350 | 600 | 1500 | manner as in Example 56. As the die, a tooth die was used. In the test, dental caries was removed and a photograph of a tooth model was taken by dental X-ray equipment and thus a photograph of a state of removal of dental caries could be easily taken.

The invention claimed is:

1. A method for producing a tooth for a dental arch model comprising an enamel portion and a dentin portion, which is used for practice treatments, wherein the method comprises steps of:
   molding pellets including an inorganic powder and a binder to form a tooth molding having a two-layered structure of an enamel portion molding and a dentin portion molding, wherein the inorganic powder of the enamel portion molding has a primary particle diameter ranging from 0.1 µm to 1.0 µm and the inorganic powder of the dentin portion molding has a primary particle diameter ranging from greater than 1.0 µm to no more than 8.0 µm;
   heating the tooth molding at high treatment to degrease the binder; and
   sintering the degreased tooth molding at a predetermined temperature to form a sintered body of the tooth for a dental arch model comprising the enamel portion and the dentin portion.

2. The method according to claim 1, wherein the inorganic powder of the enamel portion molding and the inorganic powder of the dentin portion molding are each independently selected from the group consisting of alumina-based ceramic powder, zirconia-based ceramic powder, silica-based ceramic powder, titanium oxide-based ceramic powder, aluminum nitride ceramic powder and silicon nitride ceramic powder.

3. The method according to claim 1, wherein the inorganic powder of the enamel portion molding is alumina-based ceramic powder.

4. The method according to claim 1, wherein either or both of the enamel portion molding and the dentin portion molding further contain(s) a heavy metal element oxide selected from the group consisting of SrO, BaO, ZnO, $ZnO_2$, and $La_2O_3$.

5. The method according to claim 1, wherein the sintered body of the inorganic powder constituting the enamel portion and the sintered body of the inorganic powder constituting the dentin portion each contain a void part, and
   the method further comprising a step of impregnating either or both of the void parts with a water-soluble material, a thermosoluble material or an organic material.

6. The method according to claim 1, wherein the dentin portion molding comprises a combustible tooth pulp mold, and wherein the dentin portion of the sintered body of the tooth comprises a tooth pulp portion, and
   the method further comprising a step of injecting a resin, a silicone rubber, a wax or a water-soluble material into the tooth pulp portion.

7. The method according to claim 1, wherein either or both of the enamel portion molding and the dentin portion molding is/are molded to have a false carious dental portion, and wherein either or both of the enamel portion of the sintered body of the tooth and the dentin portion of the sintered body of the tooth has/have the false carious dental portion.

8. The method according to claim 7, wherein each or both of the false carious dental portions in the enamel portion molding and in the dentin portion molding contain(s) at least any of a coloring material, fluorescent material and an X-ray contrast material.

9. The method according to claim 8, wherein the X-ray contrast material is a heavy metal element oxide selected from the group consisting of SrO, BaO, ZnO, $ZnO_2$, and $La_2O_3$.

* * * * *